US010031151B2

(12) United States Patent
Nagai et al.

(10) Patent No.: US 10,031,151 B2
(45) Date of Patent: Jul. 24, 2018

(54) ANALYSIS DEVICE AND REAGENT CONTAINER

(71) Applicant: SYSMEX CORPORATION, Kobe-shi, Hyogo (JP)

(72) Inventors: Takaaki Nagai, Kobe (JP); Yuichi Hamada, Kobe (JP); Nobuhiro Kitagawa, Akashi (JP)

(73) Assignee: SYSMEX CORPORATION, Kobe, Hyogo (JP)

( * ) Notice: Subject to any disclaimer, the term of this patent is extended or adjusted under 35 U.S.C. 154(b) by 0 days.

(21) Appl. No.: 15/164,105

(22) Filed: May 25, 2016

(65) Prior Publication Data

US 2016/0266161 A1    Sep. 15, 2016

Related U.S. Application Data

(60) Division of application No. 13/593,188, filed on Aug. 23, 2012, now Pat. No. 9,377,477, which is a
(Continued)

(30) Foreign Application Priority Data

Feb. 26, 2010 (JP) .................................. 2010-041330
Jun. 28, 2010 (JP) .................................. 2010-145879
Sep. 24, 2010 (JP) .................................. 2010-214572

(51) Int. Cl.
*G01N 21/00*      (2006.01)
*B01L 9/00*       (2006.01)
(Continued)

(52) U.S. Cl.
CPC ..... *G01N 35/1009* (2013.01); *G01N 35/0099* (2013.01); *G01N 35/00663* (2013.01);
(Continued)

(58) Field of Classification Search
USPC .................................. 422/63, 65, 66, 67, 73
See application file for complete search history.

(56) References Cited

U.S. PATENT DOCUMENTS 4,970,053 A    11/1990  Fechtner
5,075,082 A    12/1991  Fechtner
(Continued)

FOREIGN PATENT DOCUMENTS

CN    1223604 A    7/1999
CN    1407341 A    4/2003
(Continued)

OTHER PUBLICATIONS

International Search Report for International Application No. PCT/JP2011/053102, dated May 17, 2011 (4 pages).
(Continued)

*Primary Examiner* — Dean Kwak
(74) *Attorney, Agent, or Firm* — Brinks Gilson & Lione

(57) ABSTRACT

An analysis device for particle analysis, configured in such a manner that a reagent container is set in the device by inserting the reagent container from a side surface of the device toward the inside thereof, the reagent container having, near the forward end thereof, a suction pipe entrance portion into which a suction pipe can enter. The analysis device is provided with: a reagent container holding portion which holds the reagent container inserted from the suction pipe entrance portion side; and the suction pipe which enters, from above, the suction pipe entrance portion of the reagent container held by the reagent container holding portion and which sucks a reagent within the reagent container. The reagent container holding portion includes a guide member for guiding the insertion of the reagent container, which is inserted from the suction pipe entrance portion side, into the reagent container holding portion.

10 Claims, 22 Drawing Sheets

Related U.S. Application Data continuation of application No. PCT/JP2011/053102, filed on Feb. 15, 2011.

(51) Int. Cl.
   *G01N 35/10* (2006.01)
   *G01N 35/00* (2006.01)
   *G01N 35/04* (2006.01)
   *G01N 35/02* (2006.01)

(52) U.S. Cl.
   CPC ......... *G01N 35/04* (2013.01); *G01N 35/1002* (2013.01); *G01N 35/1079* (2013.01); *G01N 35/026* (2013.01); *G01N 2035/00673* (2013.01); *G01N 2035/0412* (2013.01)

(56) References Cited

U.S. PATENT DOCUMENTS

| | | | |
|---|---|---|---|
| 5,171,538 | A | 12/1992 | Tremmel et al. |
| 5,609,822 | A | 3/1997 | Carey et al. |
| 5,665,315 | A | 9/1997 | Robert et al. |
| 5,788,928 | A | 8/1998 | Carey et al. |
| 6,066,300 | A | 5/2000 | Carey et al. |
| 6,432,359 | B1 | 8/2002 | Carey et al. |
| 2002/0009393 | A1 | 1/2002 | Ishizawa et al. |
| 2003/0070498 | A1 | 4/2003 | Ohyama et al. |
| 2004/0105784 | A1* | 6/2004 | Fukuju .................. B01L 9/06 422/68.1 |
| 2004/0208787 | A1 | 10/2004 | Takahashi et al. |
| 2005/0047964 | A1 | 3/2005 | Nishida et al. |
| 2006/0211130 | A1 | 9/2006 | Macioszek et al. |
| 2007/0122910 | A1 | 5/2007 | Konrad et al. |
| 2009/0325274 | A1 | 12/2009 | Hamada et al. |
| 2010/0323396 | A1 | 12/2010 | Suzuki et al. |

FOREIGN PATENT DOCUMENTS

| | | |
|---|---|---|
| CN | 1526074 A | 9/2004 |
| CN | 1624485 A | 6/2005 |
| CN | 101161559 A | 4/2008 |
| CN | 101173955 A | 5/2008 |
| CN | 101583877 A | 11/2009 |
| DE | 3042333 A1 | 6/1982 |
| DE | 20 2008 006338 U1 | 3/2009 |
| EP | 1 420 255 A2 | 5/2004 |
| JP | 63-29255 | 2/1988 |
| JP | 03-176664 A | 7/1991 |
| JP | 08-105900 A | 4/1996 |
| JP | 09-033535 A | 2/1997 |
| JP | 10-010105 A | 1/1998 |
| JP | 10-096733 A | 4/1998 |
| JP | 2000-321283 A | 11/2000 |
| JP | 2002-055110 A | 2/2002 |
| JP | 3314629 B2 | 8/2002 |
| JP | 2003-075458 A | 3/2003 |
| JP | 2004-163319 A | 6/2004 |
| JP | 2004-226274 A | 8/2004 |
| JP | 2007-147627 A | 6/2007 |
| JP | 2008-224382 A | 9/2008 |
| WO | WO 2005/106500 A1 | 11/2005 |
| WO | WO 2009/104598 A1 | 8/2009 |

OTHER PUBLICATIONS

Written Opinion of the International Searching Authority for International Application No. PCT/JP2011/053102, dated May 17, 2011 (10 pages).

\* cited by examiner

SECTIONAL VIEW ALONG 400-400

ANALYSIS DEVICE AND REAGENT CONTAINER

RELATED APPLICATIONS

This application is a divisional of U.S. Patent Application Publication No. 2012/0321513, filed on Aug. 23, 2012, which is a continuation of PCT/JP2011/053102 filed on Feb. 15, 2011, which claims priority to Japanese Application Nos. 2010-041330 filed on Feb. 26, 2010, 2010-145879 filed on Jun. 28, 2010, and 2010-214572 filed on Sep. 24, 2010. The entire contents of these applications are incorporated herein by reference.

BACKGROUND OF THE INVENTION

Field of the Invention

The present invention relates to an analysis device analyzing a sample by sucking a reagent from a reagent container and a reagent container employed for the analysis device.

Description of the Background Art

In general, analyzers such as a biochemical analyzer, a hemocytometer and a urine particle analyzer, for example, are known as analyzers analyzing samples such as blood and urine.

In the biochemical analyzer, the number of types of reagents employed for analyzing a sample is remarkably large. If set positions for the reagents are decided for the respective types of the reagents in this case, it becomes necessary for the user to set the reagents after confirming the correspondence between the types of the reagents and the set positions one by one, and hence a set operation for the reagents is complicated.

Therefore, there is such a biochemical analyzer that the user can arbitrarily set any reagent on a vacant position of a reagent box, as a biochemical analyzer described in Japanese Patent Laying-Open No. 2000-321283, for example. The biochemical analyzer described in the aforementioned Japanese Patent Laying-Open No. 2000-321283 is configured to rotate a reagent box thereby arranging a reagent container of a prescribed type, which has been set by the user on an arbitrary position, on a dispensation position where a suction pipe is capable of dispensing the reagent so that the suction pipe can dispense the reagent from the reagent container of the prescribed type.

In a particle analyzer such as a hemocytometer or a urine particle analyzer, on the other hand, the number of measurement items is not so large as that of the biochemical analyzer, while the number of types of used reagents is also small. While a stain solution for specifically staining particles (cells) of a specific type is employed as a reagent, there is an apprehension that a carryover is caused when dispensation is performed by employing a common suction pipe in a case where there are a plurality of types of such stain solutions. Therefore, set positions for reagent containers are predetermined in response to the types of reagents, and each reagent container is configured to be fluidly connected with a prescribed portion of the analyzer. As a reagent container storing a reagent used in such an analyzer, there is a flat baggy reagent container as described in Pamphlet of International Patent Laying-Open No. 2009/104598, for example. Such a reagent container is fluidly connected with the prescribed portion of the analyzer by a flexible tube, for example, and employed.

When the user tries to set a reagent container such as that described in the aforementioned Pamphlet of International Patent Laying-Open No. 2009/104598 on an analyzer, however, it becomes necessary to detach a lid of the baggy reagent container and to insert a tube connected to the analyzer into the reagent container, and it has been accompanied by a complicated manual operation.

SUMMARY OF THE INVENTION

An analysis device according to a first aspect of the present invention is an analysis device for particle analysis, to which a reagent container is inserted from a side surface of the device and set, the reagent container having a suction pipe entrance portion into which a suction pipe is enterable in the vicinity of a forward end, and includes a reagent container holding portion configured to hold the reagent container inserted from the suction pipe entrance portion side and the suction pipe for sucking a reagent in the reagent container by entering the suction pipe entrance portion of the reagent container held by the reagent container holding portion from above, while the reagent container holding portion includes a guide member guiding the insertion of the reagent container inserted from the suction pipe entrance portion side into the reagent container holding portion.

A reagent container according to a second aspect of the present invention is a reagent container set on an analysis device by being inserted into the device from a side surface of the device, and has a suction pipe entrance portion into which a suction pipe of the analysis device is enterable from above in the vicinity of a forward end in a direction inserted into the analysis device.

An analysis device according to a third aspect of the present invention includes a reagent container holding portion for holding a reagent container, a suction pipe for sucking a reagent from the reagent container held by the reagent container holding portion, a suction pipe moving mechanism advancing the suction pipe into the reagent container held by the reagent container holding portion and retreating the suction pipe out of the reagent container and a withdrawal prevention member movable to a withdrawal position allowing withdrawal of the reagent container from the reagent container holding portion and a withdrawal prevention position preventing withdrawal of the reagent container from the reagent container holding portion, while the suction pipe moving mechanism is configured to move the suction pipe in association with movement of the withdrawal prevention member, and so configured that the suction pipe enters the reagent container held by the reagent container holding portion when the withdrawal prevention member moves to the withdrawal prevention position and the suction pipe retreats out of the reagent container when the withdrawal prevention member moves to the withdrawal position.

DETAILED DESCRIPTION OF THE PREFERRED EMBODIMENTS

Embodiments of the present invention are now described on the basis of the drawings.

First Embodiment

First, the overall structure of a blood analysis system 1 according to a first embodiment of the present invention is described with reference to FIGS. 1 to 18. In the first embodiment, a case of applying the present invention to a measurement unit of a blood analysis system (hemocytometer), which is an example of an analysis device, is described. Further, a case of applying the present invention to a reagent container employed for the measurement unit is described as an example of a reagent container according to the present invention.

Figure 1:
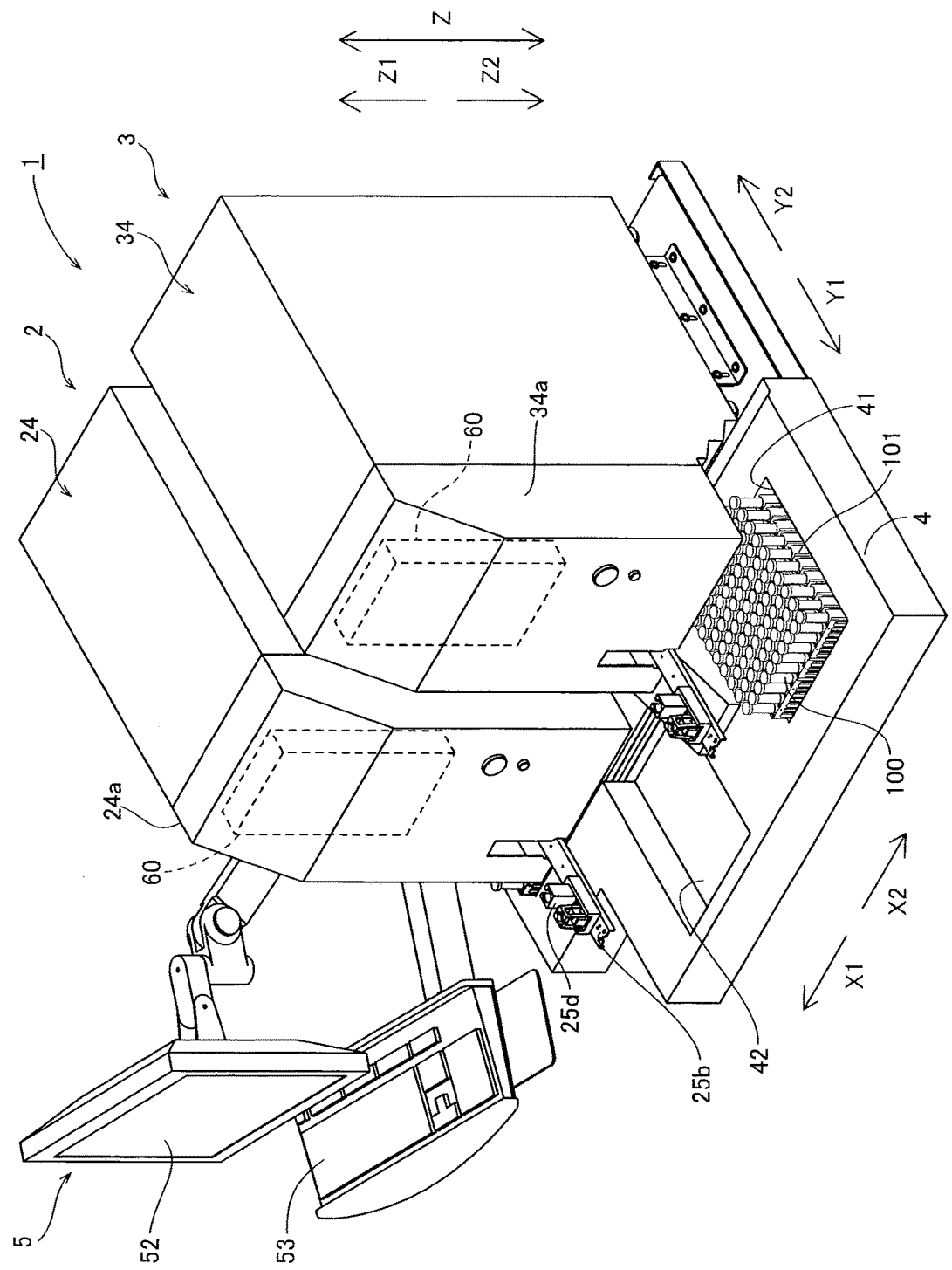
FIG. 1 is a perspective view showing a blood analysis system including a first measurement unit and a second measurement unit according to a first embodiment of the present invention.

The blood analysis system 1 according to the first embodiment includes two measurement units of a first measurement unit 3 arranged on an arrow X2 direction side and a second measurement unit 2 arranged on an arrow X1 direction side, a sample transport device (sampler) 4 arranged on a front surface side (arrow Y1 direction side) of the first measurement unit 3 and the second measurement unit 2, and a control device 5 consisting of a PC (personal computer) electrically connected to the first measurement unit 3, the second measurement unit 2 and the sample transport device 4, as shown in FIG. 1. The blood analysis system 1 is connected to a host computer 6 (see FIG. 2) by the control device 5.

Figure 2:
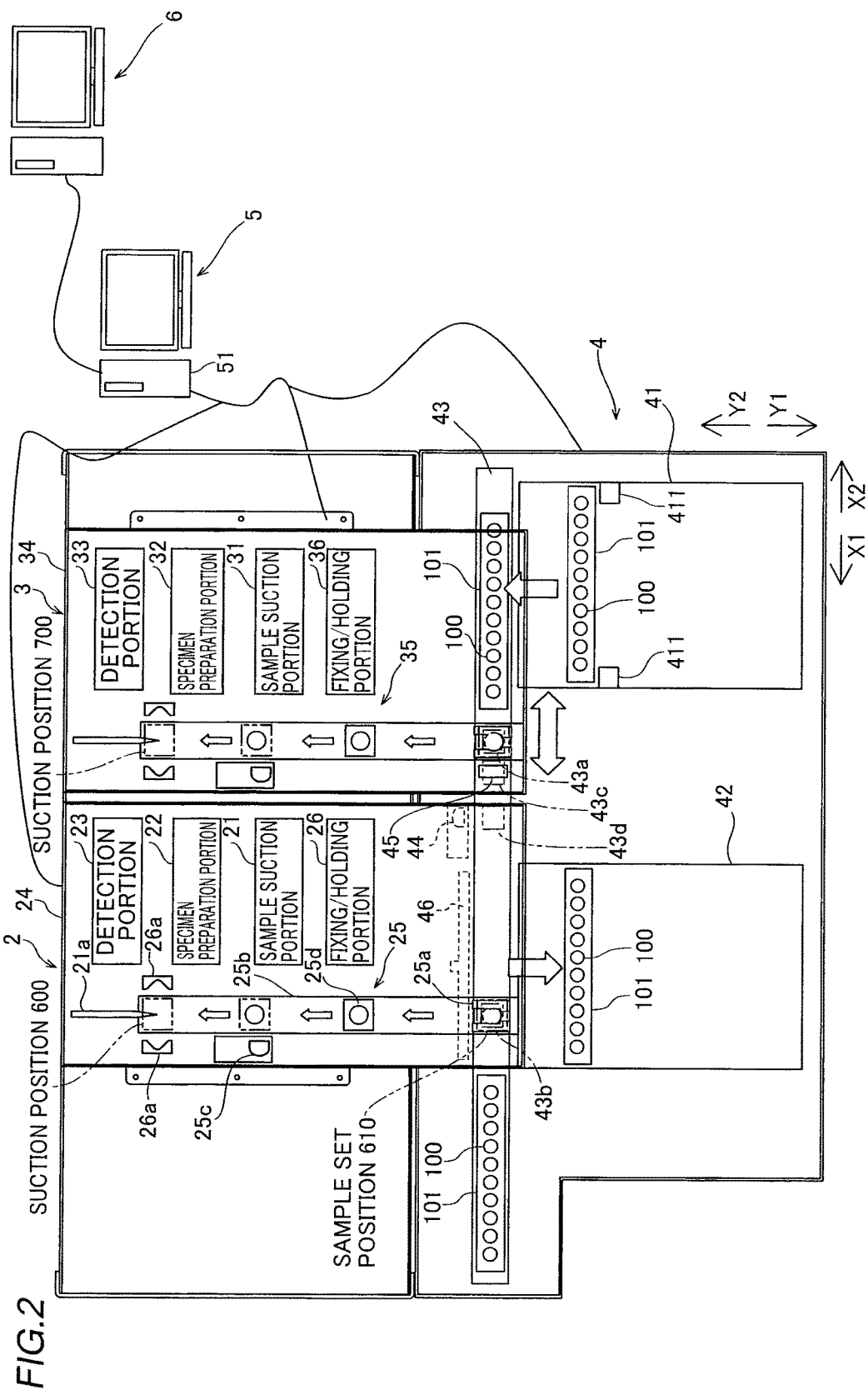
FIG. 2 is a schematic diagram showing the structure of the blood analysis system including the first measurement unit and the second measurement unit according to the first embodiment shown in FIG. 1.

As shown in FIGS. 1 and 2, the first measurement unit 3 and the second measurement unit 2 are measurement units of substantially identical types, and arranged adjacently to each other. More specifically, the second measurement unit 2 uses the same measurement principle as the first measurement unit 3 and measures samples as to the same measurement items. Further, the second measurement unit 2 measures the samples also as to measurement items not analyzed by the first measurement unit 3. As shown in FIG. 2, the second measurement unit 2 and the first measurement unit 3 include sample suction portions 21 and 31 sucking blood which is samples from sample containers (test tubes) 100, specimen preparation portions 22 and 32 preparing detection specimens from the blood sucked by the sample suction portions 21 and 31, and detection portions 23 and 33 detecting blood cells of the blood from the detection specimens prepared by the specimen preparation portions 22 and 33 respectively.

As shown in FIG. 2, the second measurement unit 2 and the first measurement unit 3 further include unit covers 24 and 34 storing the sample suction portions 21 and 31, the specimen preparation portions 22 and 32 and the like therein, sample container transport portions 25 and 35 incorporating the sample containers 100 into the unit covers 24 and 34 and transporting the sample containers 100 to suction positions 600 and 700 by the sample suction portions 21 and 31, and fixing/holding portions 26 and 36 fixing/holding the sample containers 100 on the suction positions 600 and 700 respectively. The first measurement unit 3 and the second measurement unit 2 are the measurement units of substantially identical types as described above, and hence the second measurement unit 2 is described in the following, while description is omitted as to the first measurement unit 3.

Figure 3:
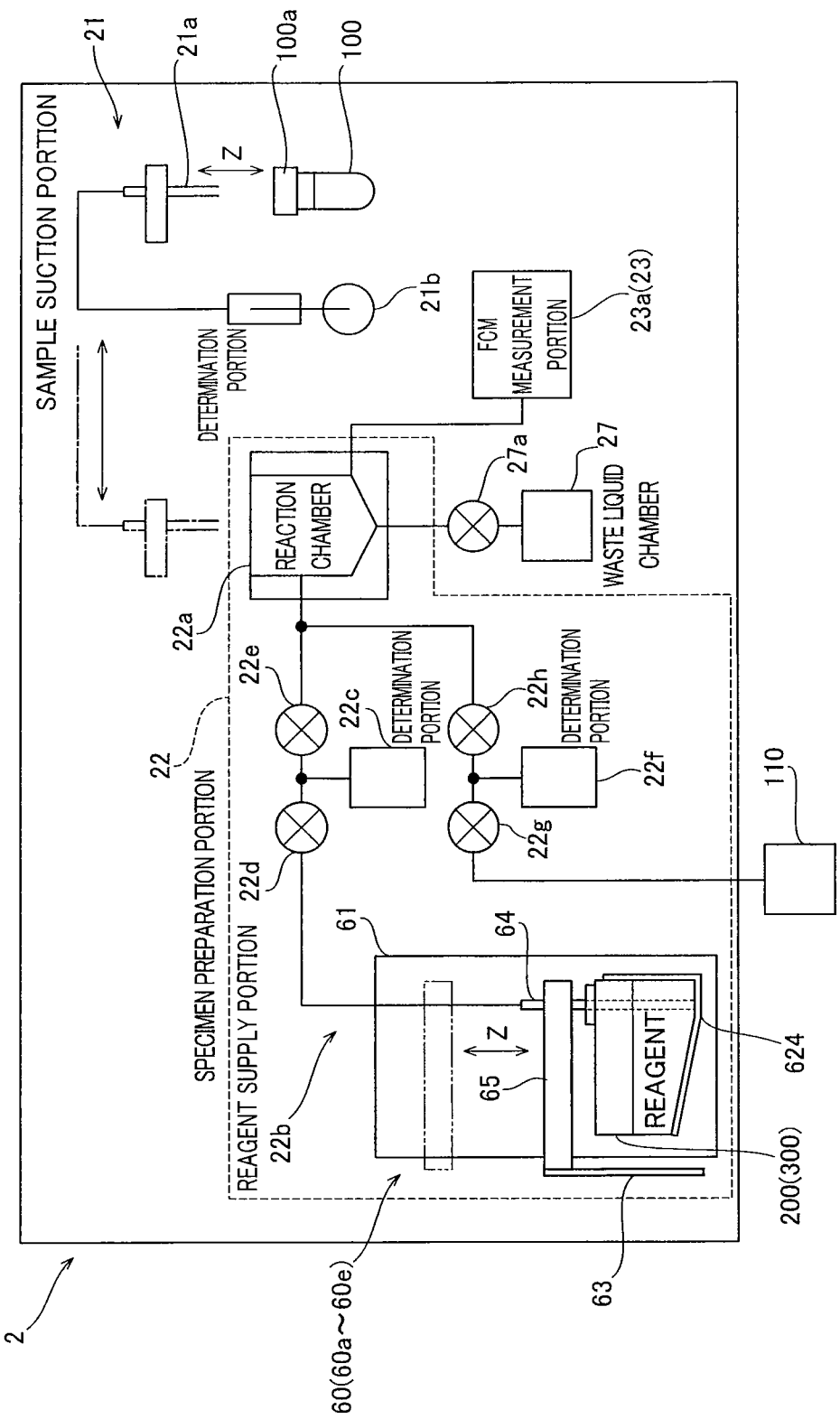
FIG. 3 is a schematic diagram showing the structure of the second measurement unit according to the first embodiment shown in FIG. 2.

The sample suction portion 21 includes a piercer 21a, which is such a suction pipe that reagents pass therethrough, and a determination portion 21b, as shown in FIG. 3. The piercer 21a is so formed that the forward end is capable of penetrating (puncturing) a closing lid 100a of each sample container 100. Further, the piercer 21a is moved by an unshown piercer driving portion in the vertical direction (direction Z), and formed to be movable up to reaction chambers 22a described later. The determination portion 21b consists of a syringe pump or the like, and has a function of sucking prescribed quantities of samples from the sample containers 100 and discharging the same through the piercer 21a. Thus, the sample suction portion 21 is so formed that the prescribed quantities of samples necessary for sample measurement are sucked from the sample containers 100 and the sucked samples are supplied to the reaction chambers 22a.

As shown in FIG. 2, the detection portion 23 includes a measurement portion (not shown) performing RBC detection (detection of red blood cells) and PLT detection (detection of platelets) by sheath flow DC detection and performing HGB detection (detection of hemoglobin in blood) by the SLS-hemoglobin method. Further, the detection portion 23 includes an FCM measurement portion 23a performing WBC detection (detection of white blood cells) by flow cytometry using a semiconductor laser, as shown in FIG. 3. Results of detection obtained by the detection portion 23 are transmitted to the control device 5 as measurement data (measurement results) of the samples.

As shown in FIG. 3, the specimen preparation portion 22 of the second measurement unit 2 includes the reaction chambers 22a and a reagent supply portion 22b connected to the reaction chambers 22a. The reaction chambers 22a are formed to mix and react samples (blood) sucked by the sample suction portion 21 and reagents supplied from the reagent supply portion 22b with each other. The reaction chambers 22a are plurally provided in response to measurement types. A plurality of types of reagents (stain solutions etc.) responsive to measurement items are supplied to each reaction chamber 22a, so that test specimens responsive to various types of measurement items are prepared through mixing and reaction processes of the samples and the reagents. Each reaction chamber 22a is so formed that the prepared test specimens are supplied to the FCM measurement portion 23a.

According to the first embodiment, the reagent supply portion 22b is provided in the unit cover 24, and holds a plurality of reagent containers 200 (see FIG. 7) or 300 (see FIG. 8) storing prescribed quantities of reagents. The reagent supply portion 22b includes a reagent container holder 60 sucking the reagents in the reagent containers 200 (or 300), a determination portion 22c consisting of a syringe pump and a diaphragm pump etc. and electromagnetic valves 22d and 22e performing opening/closing of a passage at a time of transferring the sucked reagents to the determination portion 22c and the reaction chambers 22a. Further, the reagent supply portion 22b includes a determination portion 22f and electromagnetic valves 22g and 22h for transferring a reagent (hemolytic agent or the like) from a large-volume reagent container 110 arranged outside the measurement unit, in addition to the reagent containers 200 (or 300) held by the reagent container holder 60. The reagent containers 200 and 300 are described later in detail.

As shown in FIG. 1, an openable/closable front surface cover 24a is provided on a front surface side of the unit cover 24. The reagent container holder 60 is arranged on a front surface upper portion of the second measurement unit 2, and exposed outward by opening the front surface cover 24a. Thus, the user can easily exchange the reagent containers 200 and 300. An openable/closable front surface cover 34a is also provided on a front surface side of the unit cover 34 of the first measurement unit 3. Similarly, a reagent container holder 60 is arranged on a front surface upper portion of the first measurement unit 3, and exposed outward by opening the front surface cover 34a.

Figure 4:
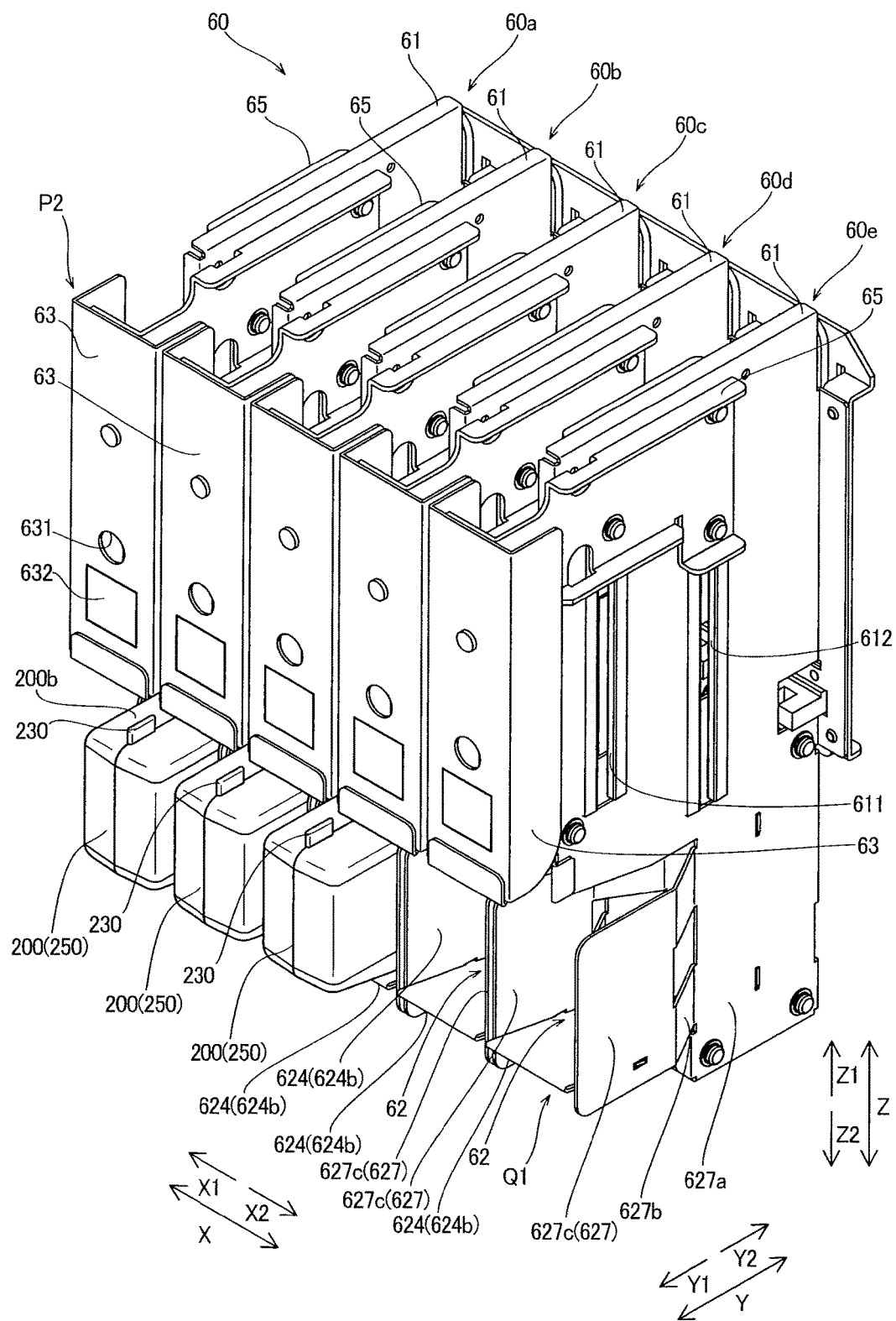
FIG. 4 is a perspective view showing a reagent container holder of the second measurement unit according to the first embodiment shown in FIG. 2.
Figure 5:
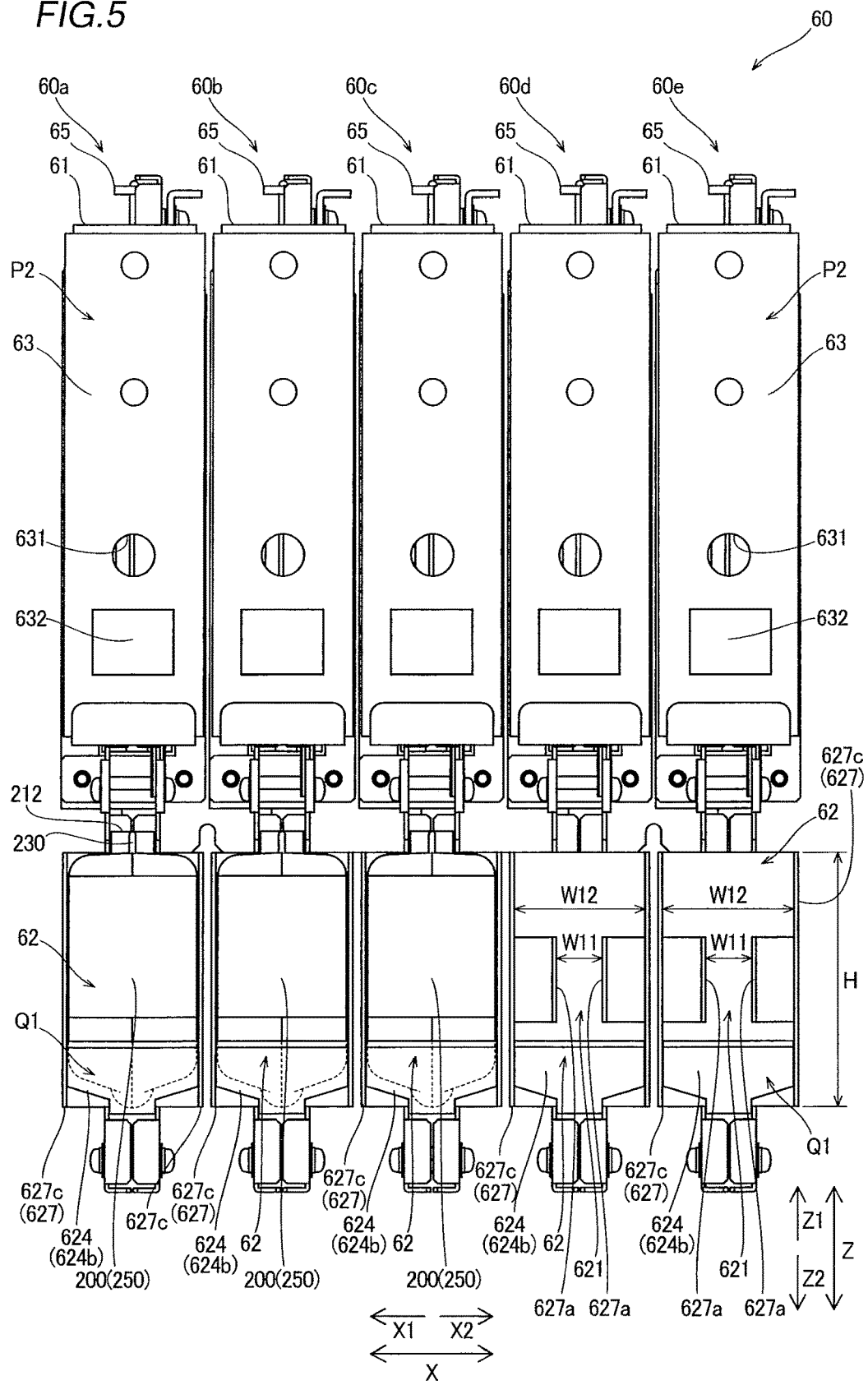
FIG. 5 is a front elevational view showing the reagent container holder shown in FIG. 4.

As shown in FIGS. 4 and 5, each reagent container holder 60 includes five holder portions 60a, 60b, 60c, 60d and 60e, and is formed to hold five (five types of) reagent containers 200 (or 300) in total. The reagent containers 200 (or 300) held by the reagent container holder 60 store reagents (stain solutions), for measuring a plurality of measurement items with the FCM measurement portion 23a, of types different from each other respectively. The color of the reagent containers is black. While the reagent containers 200 (see FIG. 12) of a large size (about 100 mL) and the reagent containers 300 (see FIG. 15) of a small size (about 20 mL) are employed as the reagent containers in response to the types of the reagents, each of the holder portions 60a to 60e is formed to be capable of holding any of the reagent containers 200 or 300. Therefore, the five holder portions 60a to 60e have similar structures respectively, and the large-sized reagent containers 200 are set on the three holder portions 60a to 60c while the small-sized reagent containers 300 (not shown in FIGS. 4 and 5) are set on the two holder portions 60d and 60e, for example. The holder portions 60a to 60e include chassis 61, reagent container holding portions 62, covers 63 for opening/closing the reagent container holding portions 62, the aforementioned piercers 64 and, piercer raising/lowering mechanisms 65 respectively.

Figure 6:
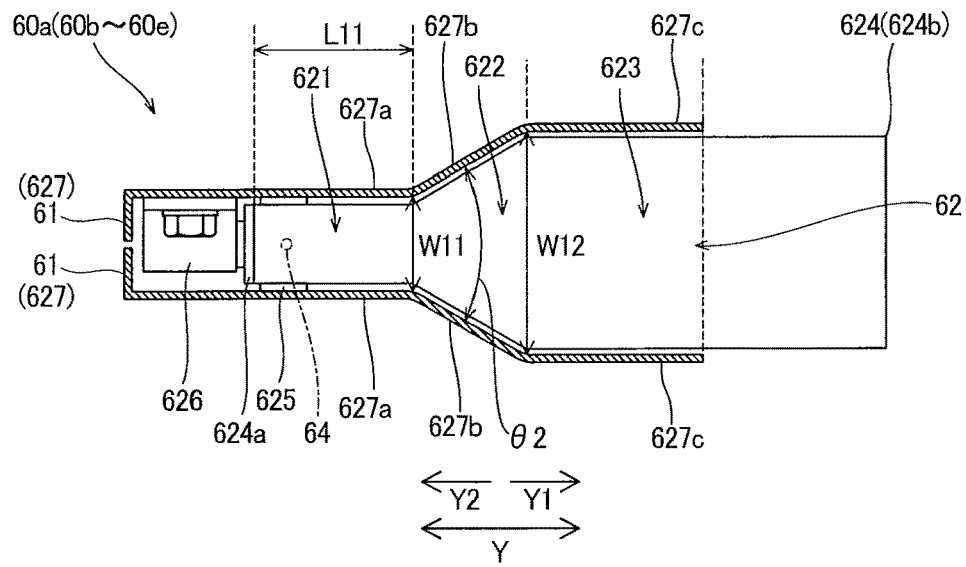
FIG. 6 is a schematic diagram for illustrating a reagent container holding portion of the reagent container holder shown in FIG. 4.
Figure 7:
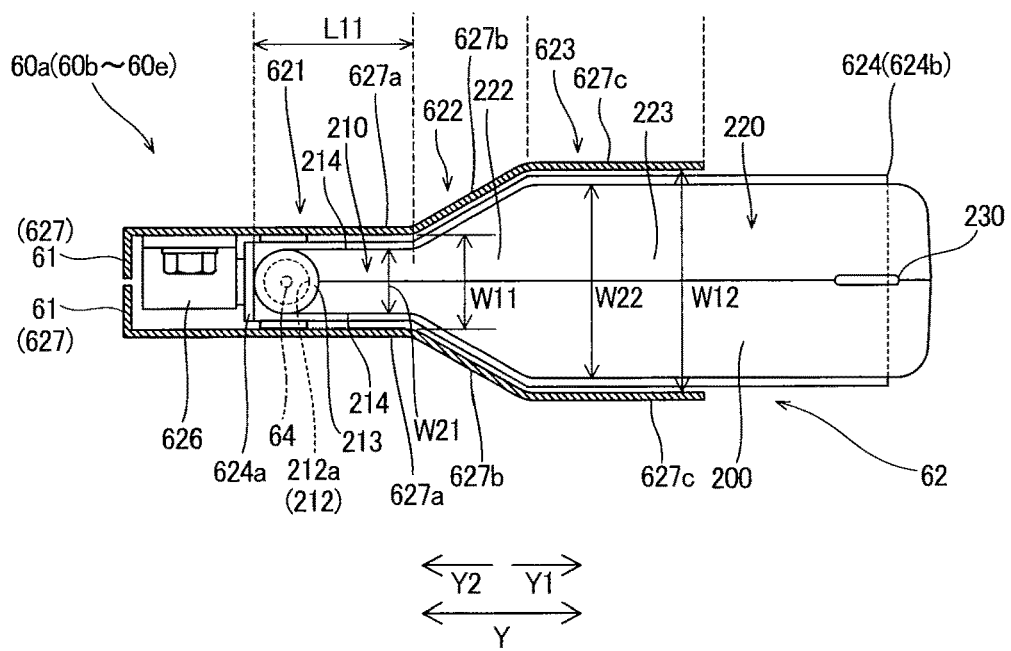
FIG. 7 is a schematic diagram showing a state where a reagent container is placed on the reagent container holding portion shown in FIG. 6.
Figure 8:
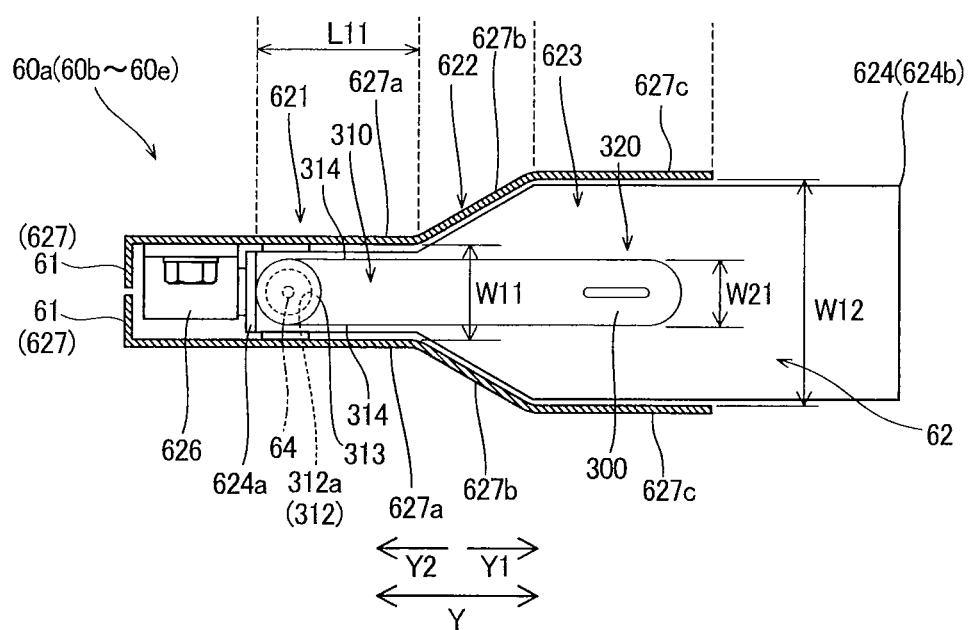
FIG. 8 is a schematic diagram showing the state where the reagent container is placed on the reagent container holding portion shown in FIG. 6.

The reagent container holding portions 62 are provided under the chassis 61 (see FIG. 5). Each reagent container holding portion 62 has a height H (see FIG. 5), and includes a first acceptance portion 621 having a width W11, an intermediate acceptance portion 622, continuous with the first acceptance portion 621, spreading from the first acceptance portion 621 at a prescribed angle θ2, and a second acceptance portion 623 continuous with the intermediate acceptance portion 622, as shown in FIG. 6. The first acceptance portion 621 is capable of accepting a first storage portion 210 (310), described later, of each reagent container 200 (300), and has a width (width W11) inhibiting entrance of the finger(s) of the user, as shown in FIGS. 7 and 8. The finger(s) denotes the finger(s) of an adult having an average thickness, and the width W11 is 10 mm in the first embodiment. The second acceptance portion 623 has a width W12 larger than the width W11. As shown in FIGS. 7 and 8, the first acceptance portion 621 is arranged on the innermost side (arrow Y2 direction side) of the reagent container holding portion 62. Each reagent container 200 (300) is inserted from the side of an entrance portion 212 (312), described later, of the first storage portion 210 (310) toward an inner back side of the reagent container holding portion 62. Therefore, the reagent container holding portion 62 is formed to hold the reagent container 200 (300) in a state where the same is so inserted that the entrance portion 212

(312) of the reagent container 200 (300) is on the innermost side (arrow Y2 direction side).

As shown in FIGS. 6 to 8, each reagent container holding portion 62 includes a pair of guide members 627 guiding both side surfaces 214 (314) of the first storage portion 210 (310) of the reagent container 200 (300) and leading the same to the first acceptance portion 621. The guide members 627 include first guide portions 627a guiding the first storage portion 210 (310) of the reagent container 200 (300) to the first acceptance portion 621, intermediate guide portions 627b corresponding to the intermediate acceptance portion 622, and second guide portions 627c guiding a second storage portion 220 (320), described later, of the reagent container 200 (300) to the second acceptance portion 623. The guide members 627 are formed by parts (both inner side surfaces) of the corresponding chassis 61. The aforementioned first acceptance portion 621, the intermediate acceptance portion 622 and the second acceptance portion 623 are formed by a space between the pair of first guide portions 627a, a space between the pair of intermediate guide portions 627b and a space between the pair of second guide portions 627b corresponding thereto respectively. Therefore, the width W11 of the first acceptance portion 621 is equal to the width of the space between the pair of first guide portions 627a, and the width W12 of the second acceptance portion 623 is equal to the width of the space between the pair of second guide portions 627c.

The pair of guide members 627 have the height H (see FIG. 5) substantially equal to a height H1 (see FIGS. 14 and 17) of both side surfaces 214 (314) of the first storage portion 210 (310) of the reagent container 200 (300), and are formed to be capable of guiding both side surfaces 214 (314) of the first storage portion 210 (310) of the reagent container 200 (300) from lower ends up to upper ends respectively. Further, the pair of guide members 627 have shapes reflecting the outer shape of the first storage portion 210 (310), and are formed to be capable of guiding the overall both side surfaces 214 (314) of the first storage portion 210 (310) of the reagent container 200 (300). The intermediate guide portions 627b and the second guide portions 627c have shapes reflecting the outer shape of each large-sized reagent container 200, and are formed to be capable of guiding both side surfaces of a forward-end-side (first storage portion 210-side) half of the second storage portion 220. The second storage portion 220 of this large-sized reagent container 200 has a width W22 larger than the width W21 of the first storage portion 210, while the first guide portions 627a are provided with the width W11 smaller than the width W22 of the second storage portion 220.

Figure 9:
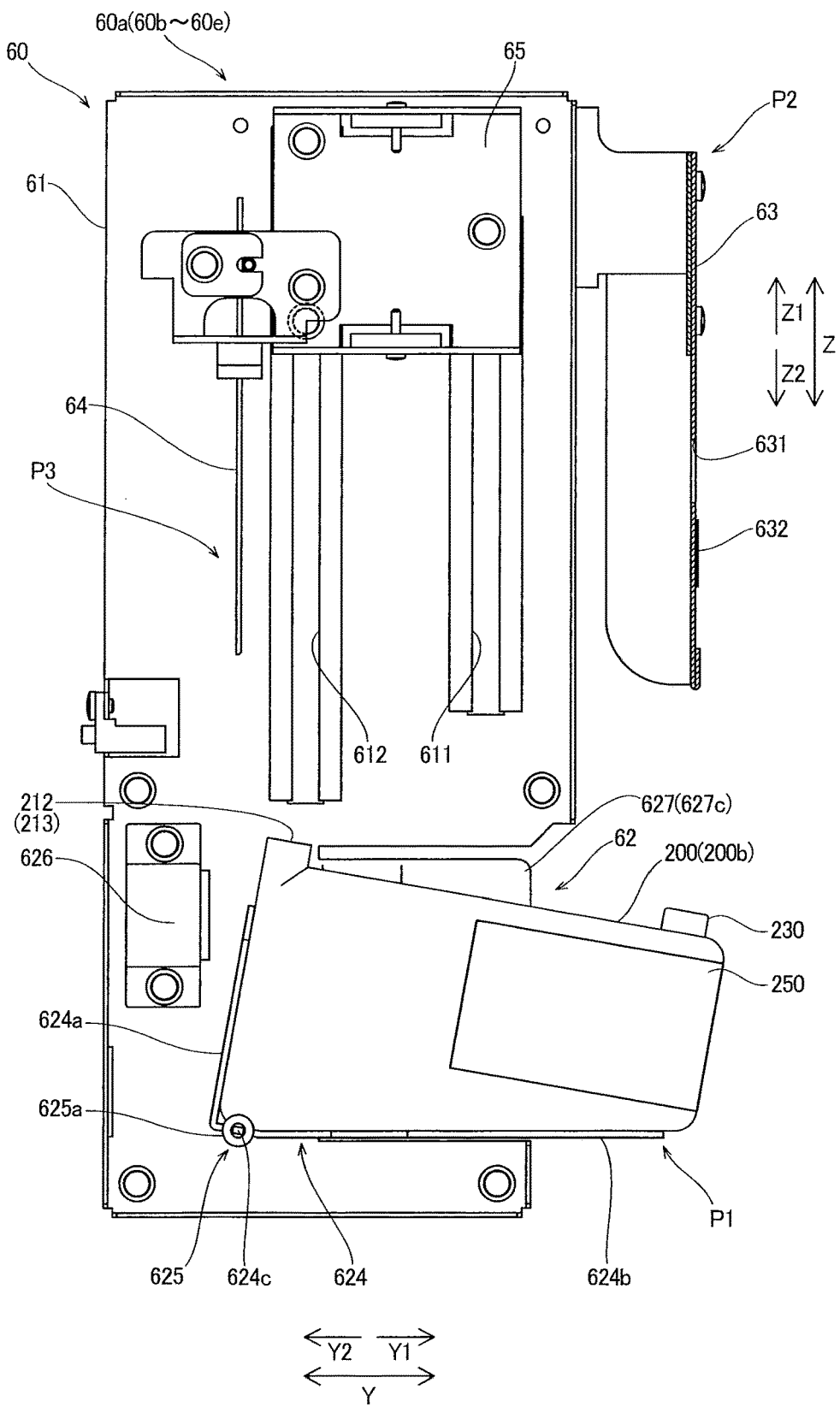
FIG. 9 is a longitudinal sectional view schematically showing the internal structure of the reagent container holder shown in FIG. 4.

As shown in FIG. 9, each reagent container holding portion 62 includes a support portion 624 holding each reagent container 200 (300) and a rotation mechanism 625 rotatably supporting the support portion 624. The support portion 624 is a platelike member integrally having a front side portion 624a coming into contact with the front surface of the reagent container 200 (300) (front end surface of the first storage portion 210 (310), see FIGS. 7 and 8) and a lower side portion 624b coming into contact with the lower surface of the reagent container 200 (300). In other words, the support portion 624 is formed to have a shape corresponding to the shape of the reagent container 200 (300). The rotation mechanism 625 is so formed that a protrusion 624c provided on the support portion 624 is inserted into an annular bearing 625a provided on the inner side surface of the chassis 61 to be capable of rotating the support portion 624 on the position, serving as a rotation center, of the protrusion 624c (bearing 625a).

A locking portion 626 locking the rotating support portion 624 by coming into contact with the front side portion 624a of the support portion 624 is provided in the chassis 61. The locking portion 626 is provided with a magnet, and so formed that the locking portion 626 holds the front side portion 624a (support portion 624) in a state in contact with the front side portion 624a of the support portion 624. Thus, the support portion 624 is formed to move to a placed position P1 (see FIG. 9) where the lower side portion 624b is horizontal (the lower surface of the reagent container 200 (300) is horizontal) and a set position Q1 (see FIG. 10) where the front side portion 624a is perpendicular. The entrance portion 212 (312) (see FIGS. 7 and 8), described later, of the reagent container 200 (300) is formed to be horizontal (orthogonal to the corresponding piercer 64) in a state where the support portion 624 is arranged on this set position Q1, as shown in FIG. 10.

Each cover 63 is arranged to protrude from each of the holder portions 60a to 60e (chassis 61) toward the front side (arrow Y1 direction side), and mounted on the corresponding piercer raising/lowering mechanism 65, as shown in FIG. 9. The cover 63 is formed to be movable to a raised position P2 (see FIG. 10) opening the reagent container holding portion 62 and a lowered position Q2 (see FIG. 11) covering (closing) the reagent container holding portion 62 due to this piercer raising/lowering mechanism 65. Therefore, the cover 63 is formed to allow introduction/withdrawal of the reagent container 200 (300) on the raised position P2 and to inhibit introduction/withdrawal of the reagent container 200 (300) on the lowered position Q2.

Figure 11:
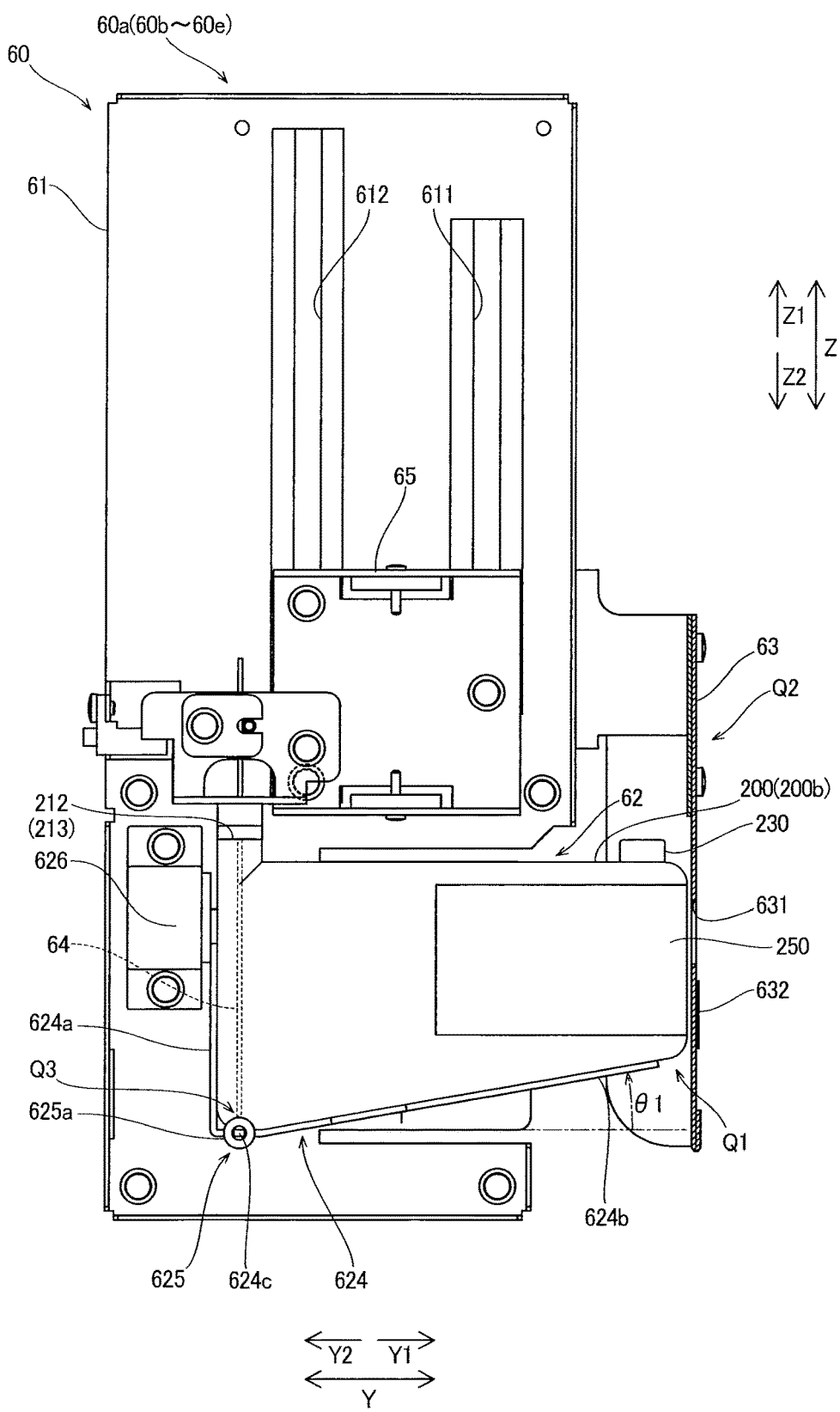
FIG. 11 is a diagram for illustrating a state lowering a cover in the longitudinal sectional view of the reagent container holder shown in FIG. 10.

As shown in FIG. 5, a window portion 631 consisting of an opening is provided on a prescribed position of each cover 63. As shown in FIG. 11, the window portion 631 is so formed that the user can visually recognize a label 250 (350, see FIG. 15) stuck to the reagent container 200 (300) through this window portion 631 in a state where the cover 63 is located on the lowered position Q2 covering (closing) the reagent container holding portion 62. An indicator for identifying the type of the reagent container 200 (300) (the type of the reagent) is printed on a position of the label 250 (350) visually recognizable through the window portion 631. A label 632, on which an indicator for identifying the type of the reagent container 200 (300) (the type of the reagent) set on the reagent container holding portion 62 is printed, is stuck to the cover 63. In other words, reagent containers 200 (300) storing determined types of reagents are set on the five holder portions 60a to 60e respectively, and hence labels 632 for identifying the types of the reagents to be set are stuck to the covers 63 of the respective holder portions 60a to 60e in correspondence thereto. Thus, the second measurement unit 2 is so formed that it is possible to confirm whether or not correct reagents are set on the respective holder portions 60a to 60e from the labels 632 provided on the covers 63 and the labels 250 (350) visually recognized through the window portions 631 in a state setting the reagent containers 200 (300) on the reagent container holding portions 62 (state lowering the covers 63 to the lowered positions Q2).

Figure 10:
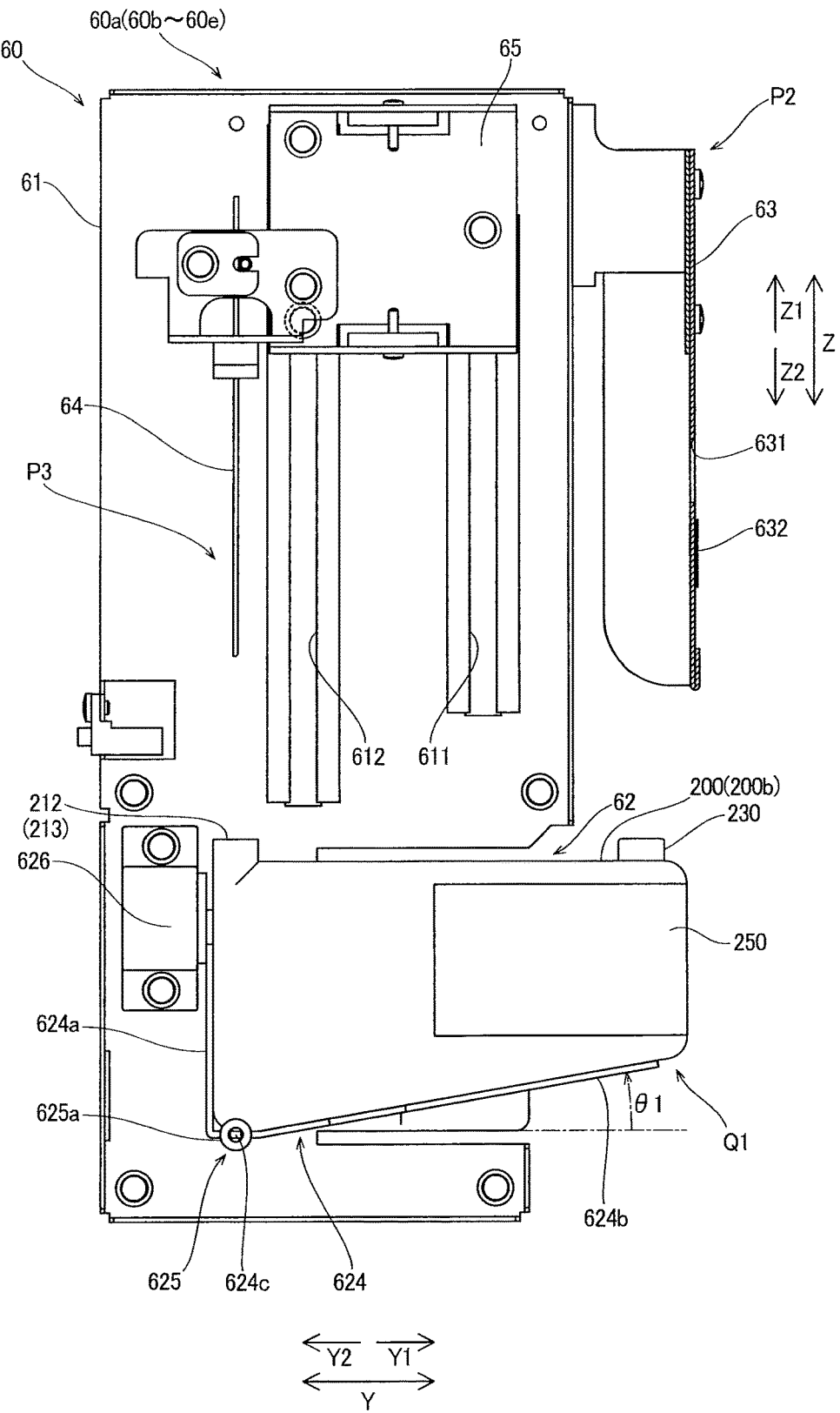
FIG. 10 a diagram for illustrating a set state of the reagent container in the longitudinal sectional view of the reagent container holder shown in FIG. 9.

As shown in FIGS. 6 and 10, each piercer 64 is arranged on a position above the innermost portion (arrow Y2 direction side) of the first acceptance portion 621 of the corresponding reagent container holding portion 62, and formed to be moved in the vertical direction (direction Z) by the piercer raising/lowering mechanism 65 holding the piercer 64. Thus, the piercer 64 is formed to enter the first storage portion 210 (310) through the entrance portion 212 (312) of the reagent container 200 (300) inserted into the inner back side of the reagent container holding portion 62 and to be capable of sucking the reagent in the reagent container 200 (300). Further, the piercer 64 is so formed that the forward end is capable of penetrating (puncturing) a sealing member 213 (313) for sealing an opening 212a (312a) (see FIGS. 7 and 8) formed in the entrance portion 212 (312) of the reagent container 200 (300). As shown in FIG. 3, the upper end of the piercer 64 is connected with the passage (illustration is omitted in FIGS. 9 to 11) reaching the determination portion 22c and the reaction chambers 22a.

As shown in FIGS. 10 and 11, the piercer raising/lowering mechanism 65 is formed to hold the piercer 64 and the cover 63. Further, the piercer raising/lowering mechanism 65 engages with groove portions 611 and 612 provided on the chassis 61 in the vertical direction (direction Z). Thus, the piercer raising/lowering mechanism 65 is formed to integrally move the piercer 64 in the vertical direction (direction Z) in association with opening/closing (raising/lowering movement) of the cover 63. In a state where the cover 63 is arranged on the raised position P2, the piercer 64 is arranged on a raised position P3 above the reagent container holding portion 62 (outside the reagent container 200 (300) and the first acceptance portion 621), as shown in FIG. 10. In a state where the cover 63 is arranged on the lowered position Q2, the piercer 64 is formed to be arranged on a lowered position Q3 approaching an inner bottom portion immediately under the entrance portion 212 (312) of the reagent container 200 (300), as shown in FIG. 11.

As shown in FIG. 3, the determination portion 22c is formed to be capable of sucking a prescribed quantity of reagent in each reagent container 200 (300) into the determination portion 22c by opening the electromagnetic valve 22d while closing the electromagnetic valve 22e in a state (see FIG. 11) arranging the piercer 64 on the lowered position Q3 in the reagent container 200 (300). Thus, the prescribed quantity of reagent necessary for preparation of a test specimen is determined. Further, the determination portion 22c is formed to be capable of transferring the reagent determined in the determination portion 22c to the reaction chambers 22a by closing the electromagnetic valve 22d while opening the electromagnetic valve 22e.

The determination portion 22f and the electromagnetic valves 22g and 22h connected with the large-volume reagent container 110 arranged outside are also similar, and the second measurement unit 2 is so formed that operations of these respective portions are so controlled that various types of reagents are transferred into the reaction chambers 22a. A waste liquid chamber 27 for disposing already measured (already prepared) specimens is provided in the second measurement unit 2, and the second measurement unit 2 is so formed that disposal of the already measured (already prepared) specimens is performed by opening/closing the electromagnetic valve 27a.

As shown in FIG. 2, the sample container transport portion 25 is formed to be linearly movable in the vertical direction (arrow Z1 and Z2 directions). The sample container transport portion 25 has a hand portion 25a capable of grasping each sample container 100, a sample container transfer portion 25b horizontally moving the sample container 100 in arrow Y1 and Y2 directions, and a bar coder read portion 25c.

The hand portion 25a is arranged above a transport path of each rack 101 transported by the sample transport device 4. Further, the hand portion 25a is formed to grasp the sample container 100 stored in the rack 101 after moving downward (arrow Z2 direction) when the sample container 100 is transported by the sample transport device 4 to a prescribed incorporation position 43b.

The hand portion 25a is capable of stirring blood in the grasped sample container 100. Further, the hand portion 25a is formed to set the sample container 100 on a sample set portion 25d moved to a sample set position 610 by the sample container transfer portion 25b after termination of stirring. As shown in FIG. 2, the incorporation position 43b and the sample set position 610 are arranged to overlap with each other in plan view.

The sample container transfer portion 25b has the sample set portion 25d, and is capable of moving the sample set portion 25d to a prescribed position responsive to an operation of measurement processing. More specifically, the sample container transfer portion 25b is capable of arranging the sample set portion 25d on the suction position 600 shown in FIG. 2 and the sample set position 610. Further, the sample container transfer portion 25b is formed to be capable of moving up to a prescribed position outside the unit cover 24 as shown in FIG. 1, so that the user manually sets the sample container 100 in a case of performing measurement of an emergency sample or a case of not using the sample transport device 4.

The bar code read portion 25c is formed to read a bar code (not shown) stuck to each sample container 100. The bar code (not shown) of each sample container 100 is specifically provided to each sample, and used for management or the like of analytical results of each sample.

The fixing/holding portion 26 is formed to fix/hold the sample container 100 transferred to the suction position 600. More specifically, the fixing/holding portion 26 has a pair of chuck portions 26a as shown in FIG. 2, and is so formed that the pair of chuck portions 26a mutually approach/move to hold the sample container 100.

The reagent containers 200 and 300 employed for the second measurement unit 2 and the first measurement unit 3 according to the first embodiment and set on the reagent container holders 60 are now described in detail.

Figure 12:
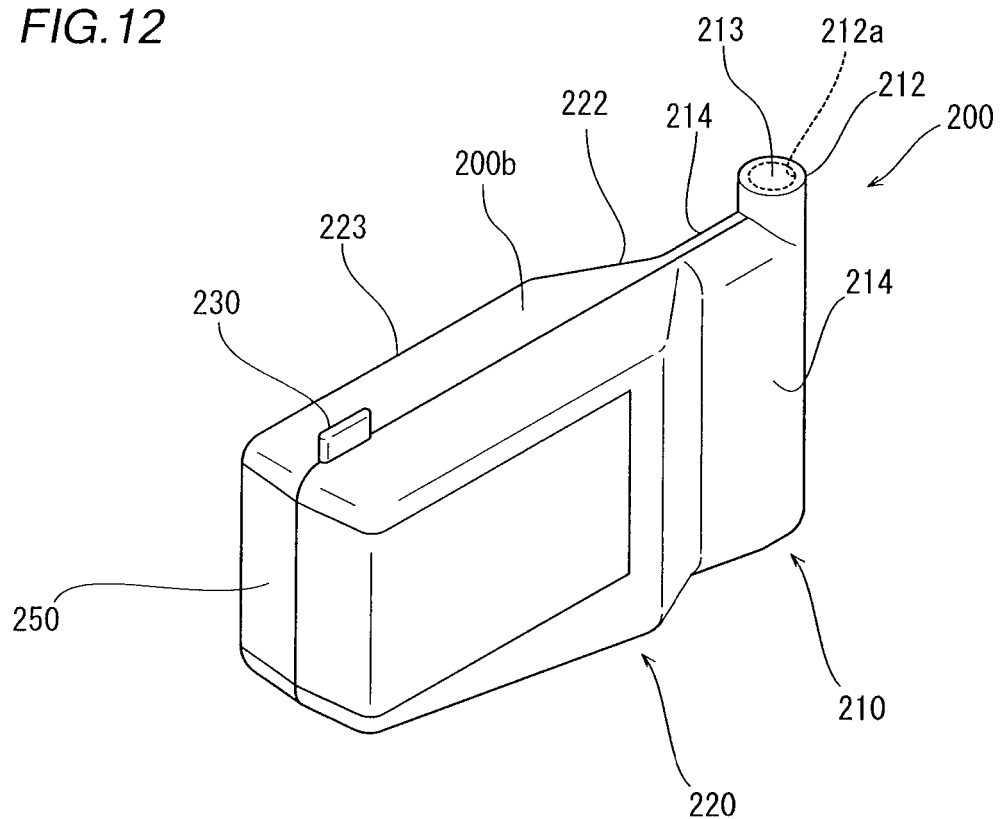
FIG. 12 is a perspective view showing a large-sized reagent container according to the first embodiment of the present invention.
Figure 14:
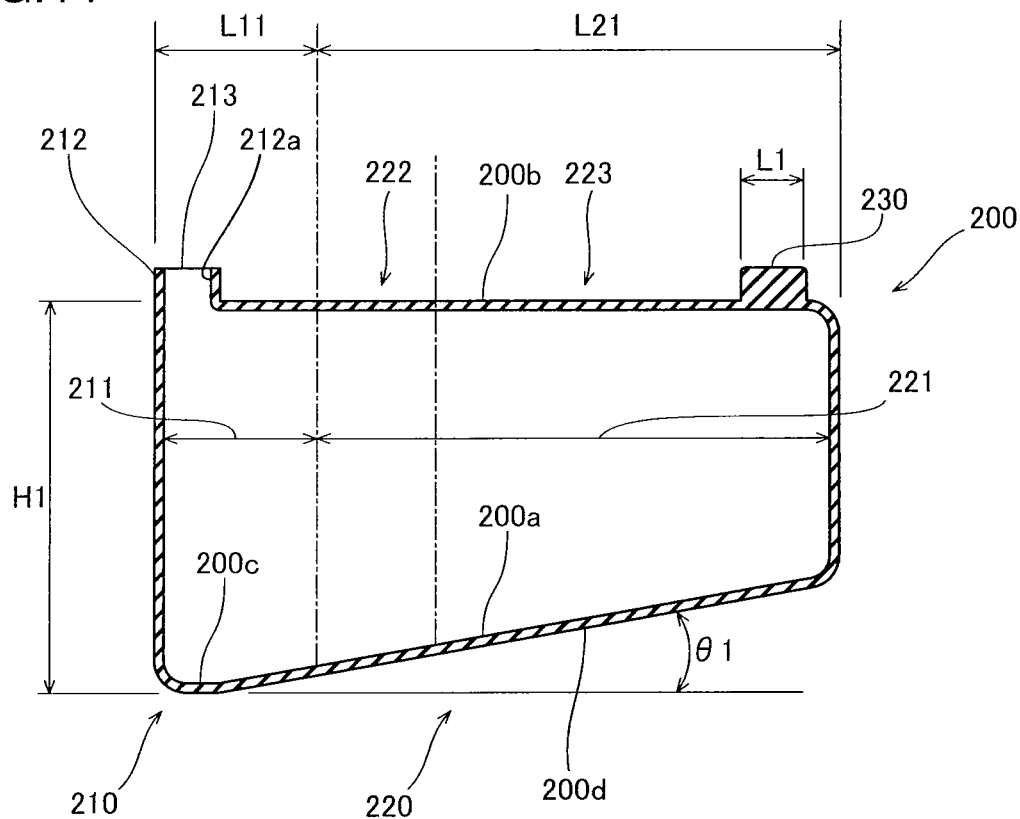
FIG. 14 is a longitudinal sectional view showing the large-sized reagent container according to the first embodiment of the present invention.
Figure 15:
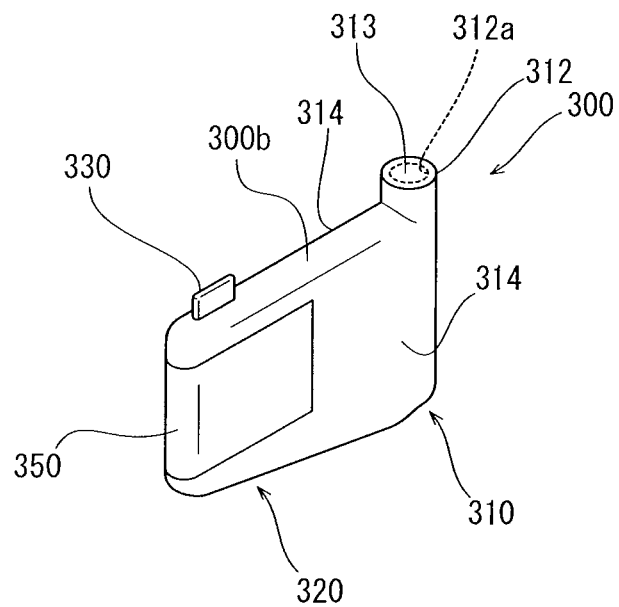
FIG. 15 is a perspective view showing a small-sized reagent container according to the first embodiment of the present invention.
Figure 17:
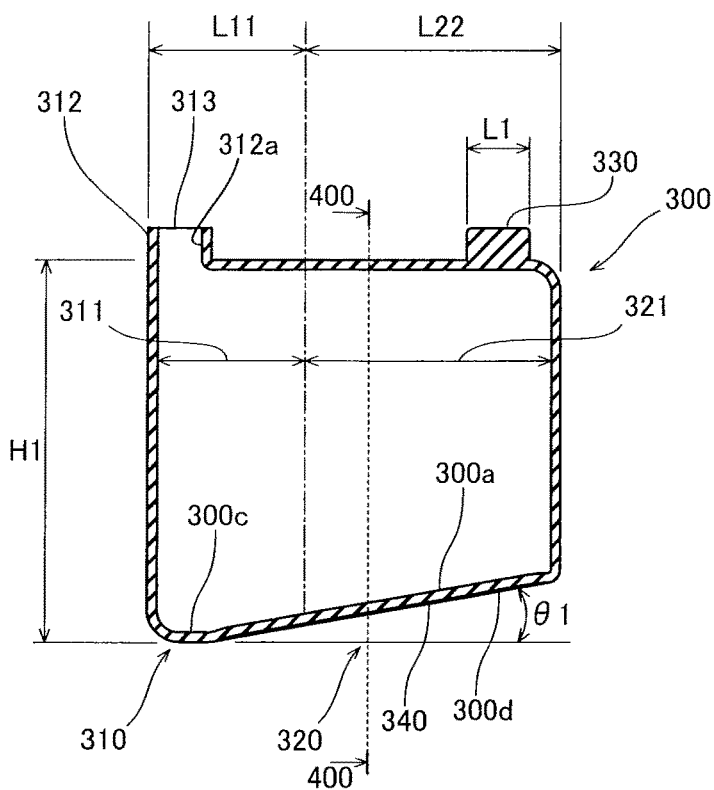
FIG. 17 is a longitudinal sectional view showing the small-sized reagent container according to the first embodiment of the present invention.
Figure 18:
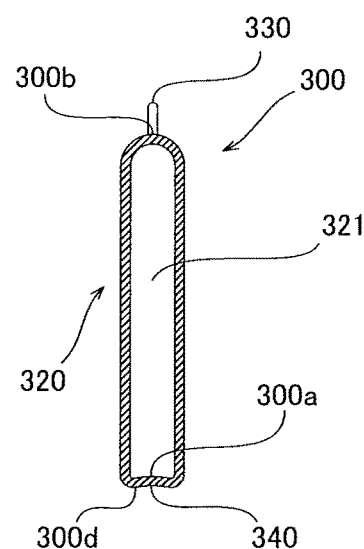
FIG. 18 is a sectional view of the small-sized reagent container according to the first embodiment of the present invention taken along the line 400-400 in FIG. 17.

According to the first embodiment, each reagent container 200 having the large size (capacity: about 100 mL) and each reagent container 300 having the small size (capacity: about 20 mL) are formed to be employed correspondingly to the types of the stored reagents, as shown in FIGS. 12 and 15. Each of the reagent containers 200 and 300 integrally includes the first storage portion 210 (310) provided on an upper portion with the entrance portion 212 (312) where the piercer 64 is enterable and the second storage portion 220 (320) continuous with the first storage portion 210 (310). The first storage portion 210 (310) is formed to be arranged in the first acceptance portion 621 in a state where the reagent container 200 (300) is set on the reagent container holding portion 62, as shown in FIGS. 7 and 8. The second storage portion 220 (320) is formed to be arranged outside the first acceptance portion 621 in the state where the reagent container 200 (300) is set on the reagent container holding portion 62, as shown in FIGS. 7 and 8. As shown in FIGS. 14 and 17, a first reagent storage space 211 (311) is provided in each first storage portion 210 (310), while a second reagent storage space 221 (321) continuous with the first reagent storage space 211 (311) is provided in each second storage portion 220 (320).

The first storage portion 210 (310) is a portion having a length L11, and this shape is substantially common in the reagent containers 200 and 300. The shapes of the first storage portions 210 and 310 are substantially common, and hence the reagent containers 200 and 300 are settable with respect to the reagent container holding portions 62 (first acceptance portions 621) of the holder portions 60*a* to 60*e* having the same shapes respectively.

More specifically, each first storage portion 210 (310) has the constant width W21 slightly smaller than the width W11 of the first acceptance portion 621, as shown in FIGS. 7 and 8. In the first storage portion 210 (310), the entrance portion 212 (312) is provided on an end portion of the front side (direction where the first storage portion 210 (310) is inserted into the reagent container holding portion 62, the arrow Y2 direction in FIGS. 7 and 8). Therefore, the reagent container 200 (300) is formed to be inserted from the side of the entrance portion 212 (312) of the first storage portion 210 (310) toward the inner back side of the reagent container holding portion 62. This entrance portion 212 (312) is provided to protrude upward from an outer upper surface 200*b* (300*b*), as shown in FIGS. 14 and 17. The opening 212*a* (312*a*) communicating with the interior of the first storage portion 210 (310) is formed in the protruding entrance portion 212 (312), as shown in FIGS. 12 and 15. The sealing member 213 (313) made of aluminum foil or the like is provided on the entrance portion 212 (312) to block the opening 212*a* (312*a*), and so formed that the reagent container 200 (300) is sealed. The outer diameter of the entrance portion 212 (312) is equal to the width W21 of the first storage portion 210 (310), and the entrance portion 212 (312) is formed to protrude continuously (flushly) from a front-side surface of the first storage portion 210 (310).

As shown in FIGS. 14 and 17, the reagent container 200 (300) is so formed that an inner bottom surface 200*a* (300*a*) is unparallel to the outer upper surface 200*b* (300*b*) and the distance between the inner bottom surface 200*a* (300*a*) and the outer upper surface 200*b* (300*b*) enlarges as approaching the entrance portion 212 (312). According to the first embodiment, the reagent container 200 (300) is so formed that the inner bottom surface 200*a* (300*a*) becomes an inclining surface inclining by an angle θ1 (about 10 degrees) with respect to the outer upper surface 200*b* (300*b*). A bottom portion 200*c* (300*c*) substantially parallel to the outer upper surface 200*b* (300*b*) is present on a bottom surface portion of the reagent container 200 (300) immediately under the entrance portion 212 (312), and an inclining surface 200*d* (300*d*) starts from an end portion of the bottom portion 200*c* (300*c*). Thus, the reagent container 200 (300) is so formed that the entrance portion 212 (312) is positioned uppermost while the bottom portion 200*c* (300*c*) immediately under the entrance portion 212 (312) is positioned lowermost in the state set on the set position Q1 shown in FIG. 10.

A protrusion 230 (330) protruding upward (perpendicular direction with respect to the outer upper surface 200*b* (300*b*)) is provided on the outer upper surface 200*b* (300*b*) of the reagent container 200 (300). The protrusion 230 (330) has a platelike shape of a length L1 extending in the longitudinal direction of the reagent container 200 (300), and is formed to have a quantity of protrusion (protrusion height) substantially equal to that of the entrance portion 212 (312). The protrusion 230 (330) is provided on a position in the vicinity of an end portion of a rear side (arrow Y1 direction side in FIGS. 7 and 8) of each second storage portion 220 (320), and has a function as a handle portion so that a set operation or a removing operation of the reagent container 200 (300) by the user can be easily performed.

On the other hand, shapes of the second storage portions 220 (320) vary with each reagent container 200 and each reagent container 300.

Figure 13:
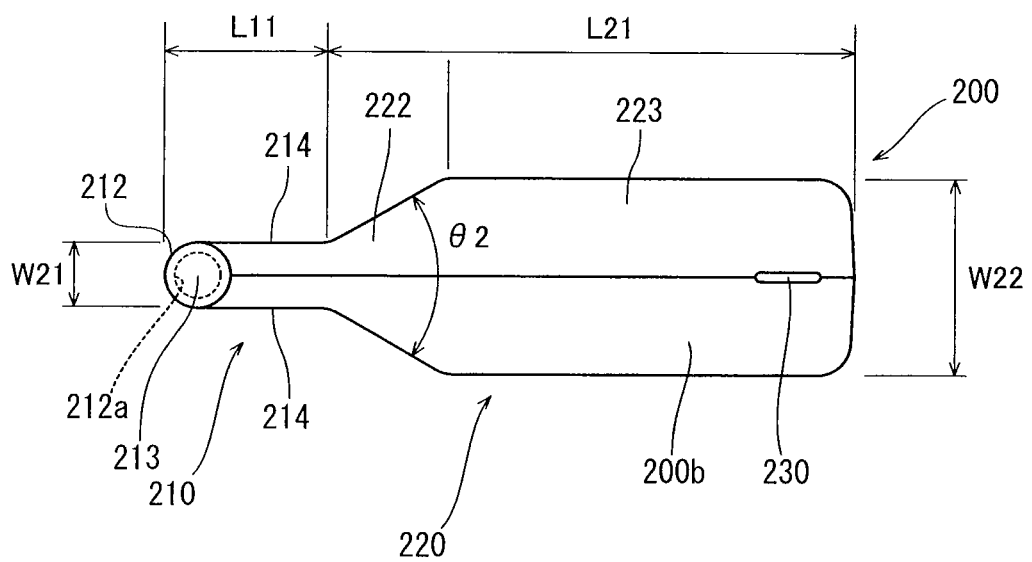
FIG. 13 is a top plan view showing the large-sized reagent container according to the first embodiment of the present invention.

As shown in FIG. 13, the second storage portion 220 of each large-sized reagent container 200 integrally includes a first portion 222, continuous with the first storage portion 210, whose width enlarges as separating from the first storage portion 210, and a second portion 223 having the constant width W22 larger than the width W21. Therefore, the second reagent storage space 221 in the second storage portion 220 is a reagent storage space continuously provided over both of the first portion 222 and the second portion 223 in the reagent container 200, as shown in FIG. 14.

As shown in FIG. 13, the first portion 222 is continuous with the second portion 223 to expand the width of the first storage portion 210 at the angle 2 (about 60 degrees), and connects the first storage portion 210 and the second portion 223 with each other. The second storage portion 220 is so formed that the second portion 223 has the width W22 larger than the width W21 so that the capacitance of the second reagent storage space 221 can be ensured by about 100 mL.

As shown in FIGS. 6 and 7, the intermediate acceptance portion 622 of the reagent container holding portion 62 and the second acceptance portion 623, continuous with the intermediate acceptance portion 622, having the width W12 have shapes corresponding to this first portion 222 and the second portion 223 having the width W22 respectively.

Figure 16:
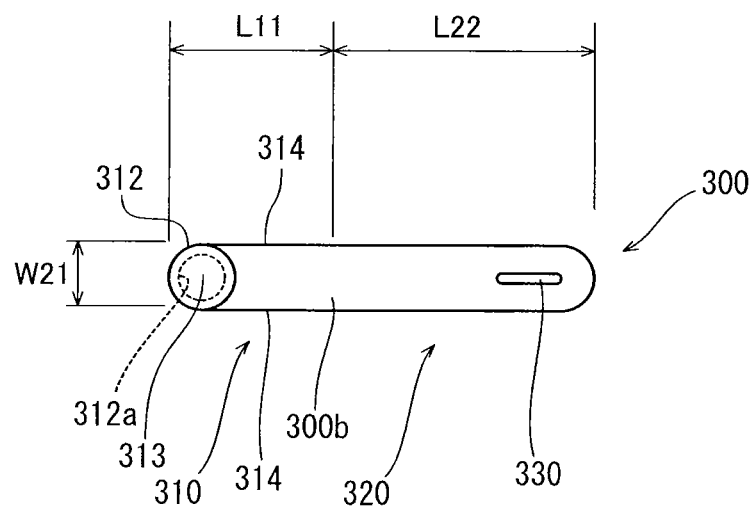
FIG. 16 is a top plan view showing the small-sized reagent container according to the first embodiment of the present invention.

As shown in FIG. 16, the second storage portion 320 of each small-sized reagent container 300 has the width W21, which is constant and identical to the width W21 of the first storage portion 310. In other words, the first storage portion 310 and the second storage portion 320 are formed to continuously linearly extend in the small-sized reagent container 300. The length L22 of this second storage portion 320 is smaller than the length L21 of the second storage portion 220 of the large-sized reagent container 200. The small-sized reagent container 300 is formed to have a reagent capacitance of about 20 mL as a whole by including the second storage portion 320 having the width W21 and the length L22 smaller than those of the second storage portion 220 of the large-sized reagent container 200.

As hereinabove described, the length L11 of the first storage portion 310 is common in the reagent containers 200 and 300, to be set on the first acceptance portion 621. As to the small-sized reagent container 300 in which the first storage portion 310 and the second storage portion 320 are continuous with each other in the same width W21 as shown in FIG. 8, therefore, a region stored in this first acceptance portion 621 is the first storage portion 310, and a region arranged outside the first acceptance portion 621 is the second storage portion 320.

In the small-sized reagent container 300, a recess portion 340 linearly extending along the longitudinal direction of the reagent container 300 is provided on the inclining surface 300*d* of the outer bottom surface, dissimilarly to the large-sized reagent container 200. In a case of setting the inclining surface 300*d* on a horizontal plane, an outer peripheral portion of the recess portion 340 becomes a point of contact in contact with the horizontal plane due to this recess portion 340, whereby it is possible to stably upright the reagent container 300 having the small width W21 as well.

As shown in FIGS. 12 and 15, the label 250 (350), on which the name of the stored reagent, the lot number of the reagent, the expiration date and an identification bar code etc. are printed, is stuck to each reagent container 200 (300). This label 250 (350) is stuck over the rear surface of each reagent container 200 (300) and at least one lateral side surface. Further, coloring indicating the type of the stored reagent is applied to part (portion corresponding to the rear surface of each reagent container 200 (300)) or the whole of the label 250 (350), and the reagent container 200 (300) is so formed that it is possible to identify the type of the reagent through the color displayed on the label 250 (350). It is possible to confirm whether or not the reagent container 200 (300) has been set on the correct one of the holder portions 60*a* to 60*e*, depending on whether the colors of the respective ones of this label 250 (350) and the label 632 (see FIG. 5) stuck to the cover 63 of the reagent container holder 60 coincide with each other.

As shown in FIGS. 1 and 2, the sample transport device 4 includes a pre-analysis rack holding portion 41 capable of holding a plurality of racks 101 in which sample containers 100 storing samples before performance of analysis, a post-analysis rack holding portion 42 capable of holding a plurality of racks 101 in which sample containers 100 storing samples after performance of analysis, a rack transport portion 43 horizontally linearly moving the racks 101 in arrow X1 and X2 directions, a bar code read portion 44, a presence/absence detection sensor 45 sensing the presence or absence of the sample containers 100, and a rack delivery portion 46 moving the racks 101 into the post-analysis rack holding portion 42.

The pre-analysis rack holding portion 41 has a rack feeding portion 411, and is so formed that the rack feeding portion 411 moves in the arrow Y2 direction thereby pushing out the racks 101 held by the pre-analysis rack holding portion 41 one by one onto the rack transport portion 43.

The rack transport portion 43 is formed to arrange prescribed sample containers 100 held on the racks on an incorporation position 43*a* where the first measurement unit 3 incorporates samples and the incorporation position 43*b* where the second measurement unit 2 incorporates samples by transporting the racks 101, as shown in FIG. 2. Further, the rack transport portion 43 is formed to be capable of transporting the sample containers 100 to a sample presence/absence detection position 43*c* where the presence/absence detection sensor 45 confirms the presence or absence of the sample containers 100 and a read position 43*d* where the bar code read portion 44 reads the bar codes (not shown) (see FIG. 4) of the sample containers 100.

The rack delivery portion 46 is arranged to be opposed to the post-analysis rack holding portion 42 through the rack transport portion 43, and formed to horizontally move in the arrow Y1 direction. Further, the rack delivery portion 46 is formed to push out each rack 101 arranged on a position held between the post-analysis rack holding portion 42 of the rack transport portion 43 and the rack delivery portion 46 to the side of the post-analysis rack holding portion 42 by horizontally moving in the arrow Y1 direction.

The control device 5 consists of a personal computer (PC) or the like, and is mainly constituted of a control portion 51 (see FIG. 2) consisting of a CPU, a ROM, a RAM and the like, a display portion 52 and an input device 53, as shown in FIGS. 1 and 2. The display portion 52 is provided for displaying analytical results or the like obtained by analyzing data of digital signals transmitted from the first measurement unit 3 and the second measurement unit 2.

The control portion 51 includes the CPU, the ROM, the RAM, a hard disk, an input/output interface and a communication interface etc., and the CPU so runs application programs that the computer functions as the control device 5. Thus, the control device 5 is so formed that operations of respective portions of the first measurement unit 3, the second measurement unit 2 and the sample transport device 4 are controlled by the control portion 51. A measurement result database is also installed in the hard disk of the control portion 51.

The control portion 51 is formed to analyze components of analytical objects by employing measurement results transmitted from the first measurement unit 3 and the second measurement unit 2 and to acquire analytical results (the number of red blood cells, the number of platelets, the quantity of hemoglobin, the number of white blood cells etc.).

An operation of setting each reagent container 200 on the reagent container holder 60 (holder portion 60*a*) of each of the first measurement unit 3 and the second measurement unit 2 according to the present invention is now described with reference to FIGS. 7, 9 to 11 and 14. Set operations are similar to each other in the reagent containers 200 and 300, and hence only the set operation for the reagent container 200 is described, while the set operation for the reagent container 300 is omitted. Similarly, only the set operation for the reagent container 200 onto the holder portion 60*a* is described, and set operations onto the remaining holder portions 60*b* to 60*e* are omitted.

First, the user opens the front surface cover 24*a* (see FIG. 1), arranges the cover 63 on the raised position P2 (see FIG. 9), and opens the reagent container holding portion 62. Then, the user arranges the support portion 624 of the holder portion 60*a* on the placed position P1 (see FIG. 9) where the lower side portion 624*b* is horizontal. As the cover 63 is arranged on the raised position P2, the corresponding piercer 64 is arranged on the raised position P3 above the reagent container holding portion 62.

Then, the user places the reagent container 200 on the support portion 624. The reagent container 200 is so placed on the lower side portion 624*b* that an inclining portion (portion of the inclining surface 200*d*) of the reagent container 200 is horizontal. At this time, the entrance portion 212 (opening 212*a*) is arranged on the uppermost (arrow Z1 direction) position (see FIG. 9) of the reagent container 200.

As shown in FIG. 9, the user advances the first storage portion 210 into the first acceptance portion 621 until the front side (arrow Y2 direction side) surface of the first storage portion 210 comes into contact with the front side portion 624*a* of the support portion 624. At this time, the first storage portion 210 is inserted into the first acceptance portion 621, while overall both side surfaces 214 of the first storage portion 210 are guided along the pair of first guide portions 627*a* reflecting the shape of the first storage portion 210. Further, the second storage portion 220 is guided by the second guide portions 627*c*. Therefore, the finger(s) of the user is prevented from entering the inner back side of the reagent container holding portion 62 from a space between the reagent container 200 (respective side surfaces of the first storage portion 210 and the second storage portion 220) and the guide member 627 (the first guide portions 627*a* and the second guide portions 627*c*) in the insertion of the reagent container 200. Thus, the finger(s) of the user avoids touching the piercer 64 arranged on the raised position P3 outside (above) the reagent container holding portion 62.

Then, the user pushes the lower side portion 624*b* of the support portion 624 upward, and rotates the support portion 624 until the front side portion 624*a* comes into contact with the locking portion 626. When the front side portion 624*a* comes into contact with the locking portion 626, the support portion 624 is held on the set position Q1 where the front side portion 624*a* is perpendicular due to the magnet of the locking portion 626, as shown in FIG. 10. At this time, the reagent container 200 in the reagent container holding portion 62 is held in a state where the entrance portion 212 (opening 212*a*) and the outer upper surface 200*b* are horizontal, as shown in FIGS. 7 and 10.

Thereafter the user moves (lowers) the cover 63 of the holder portion 60*a* from the raised position P2 to the lowered position Q2, as shown in FIG. 11. The piercer 64 also lowers following this, whereby the piercer 64 passes through the sealing member 213 sealing the opening 212a (entrance portion 212) of the reagent container 200 and enters the reagent container 200 through the opening portion 212a (entrance portion 212). When the cover 63 is arranged on the lowered position Q2 by the user, the piercer 64 is arranged on the lowered position Q3 in the vicinity of the bottom portion 200c (see FIG. 14) in the reagent container 200. Thus, it becomes possible to suck the reagent in the reagent container 200 through the piercer 64.

In this state, the user is enabled to visually recognize the label 250 of the reagent container 200 from the window portion 631 of the cover 63, whereby the user is enabled to confirm whether or not the correct reagent container 200 is set from the label 632 stuck to the cover 63 and the label 250 of the reagent container 200.

Thus, the set operation for the reagent container 200 onto the reagent container holder 60 (holder portion 60a) terminates.

A measurement processing operation of the blood analysis system 1 according to the first embodiment is now described with reference to FIGS. 2 and 3. Components of analytical objects are similarly measured in the first measurement unit 3 and the second measurement unit 2 respectively, and hence a case of measuring components of analytical objects with the second measurement unit 2 is described below, while description of a measurement processing operation with the first measurement unit 3 is omitted. Measurement processing operation control of this second measurement unit 2 is performed by the control device 5.

First, the sample is sucked by the sample suction portion 21 from each sample container 100 transported to the suction portion 600 (see FIG. 2), while determined samples are supplied to the reaction chambers 22a of the specimen preparation portion 22 respectively, as shown in FIG. 3. Then, detection specimens are prepared from the sucked sample by the specimen preparation portion 22. More specifically, reagents contained in the five (five types of) reagent containers 200 (or 300) set on the reagent container holder 60 are supplied to prescribed reaction chambers 22a responsive to measurement items respectively, due to operations of the determination portion 22c and the electromagnetic valve 22d (22e). Further, the reagent (hemolytic agent or the like) stored in the external large-volume reagent container 110 is supplied to a prescribed reaction chamber 22a, due to operations of the determination portion 22f and the electromagnetic valve 22g (22h). Then, the samples and the reagents are mixed with each other in the reaction chambers 22a, and the detection specimens are prepared through a reaction process.

Then, the components of the analytical objects are detected from the detection specimens by the detection portion 23. The detection specimens prepared by employing the reagents stored in the aforementioned five (five types of) reagent containers 200 (or 300) are supplied to the FCM measurement portion 23a, and measurement of various types of measurement items by flow cytometry is performed. After termination of the measurement, the already measured detection specimens in the reaction chambers 22a are discarded to the waste liquid chamber 27 through the electromagnetic valve 27a. Then, measurement data are transmitted from the second measurement unit 2 to the control device 5. Thereafter the components of the analytical objects are analyzed by the control portion 51 on the basis of measurement results transmitted from the second measurement unit 2. Thus, analysis of the samples is completed, and the operation is terminated.

According to the first embodiment, as hereinabove described, the reagent container holding portions 62 holding the reagent containers 200 (300) inserted from the sides of the entrance portions 212 (312) in the vicinity of the forward ends and the piercers 64 entering the entrance portions 212 (312) of the reagent containers 200 (300) held by the reagent container holding portions 62 from above are provided while the guide members 627 guiding the insertion of the reagent containers 200 (300) inserted from the sides of the entrance portions 212 (312) into the reagent container holding portions 62 are provided on the reagent container holding portions 62, whereby the piercers 64 can be advanced into the reagent containers 200 (300) through the entrance portions 212 (312) inserted into the inner back sides of the reagent container holding portions 62. Therefore, the user can set the reagent containers 200 (300) by simply grasping the reagent containers 200 (300) and inserting the same into the reagent container holding portions 62 from the sides of the entrance portions 212 (312) in the vicinity of the forward ends. Thus, the set operation for the reagent containers 200 (300) can be simplified. Further, entrance of the piercers 64 into the reagent containers 200 (300) and retreat from the reagent containers 200 (300) can be performed on the inner back sides of the reagent container holding portions 62 into which the entrance portions 212 (312) are inserted, whereby the finger(s) of the user can avoid touching the piercers 64 when setting the reagent containers 200 (300). In addition, the reagent containers 200 (300) are guided to the reagent container holding portions 62 along the guide members 627, whereby the finger(s) of the user can avoid entering the inner back sides of the reagent container holding portions 62 from the spaces between the reagent containers 200 (300) and the guide members 627 when setting the reagent containers 200 (300). Thus, the finger(s) of the user can more reliably avoid touching the piercers 64.

According to the first embodiment, as hereinabove described, each guide member 627 has the height dimension H substantially identical to at least the height H1 of both side surfaces 214 (314) of the first storage portion 210 (310), and is formed to be capable of guiding both side surfaces 214 (314) of the first storage portion 210 (310) from the lower ends up to the upper ends respectively. When forming the second measurement unit 2 (the first measurement unit 3) in this manner, the guide member 627 guides both side surfaces 214 (314) of the first storage portion 210 (310) from the lower ends up to the upper ends, whereby the finger(s) of the user can avoid entering the inner back side of each reagent container holding portion 62 from the upper ends up to the lower ends of both side surfaces 214 (314) of the first storage portion 210 (310). Thus, the finger(s) of the user can more reliably avoid touching the piercer 64.

According to the first embodiment, as hereinabove described, each guide member 627 (first guide portion 627a) has the shape reflecting the shape of at least the first storage portion 210 (310) of each reagent container 200 (300), and is formed to be capable of guiding the whole of both side surfaces 210 (314) of the first storage portion 210 (310). When forming the second measurement unit 2 (the first measurement unit 3) in this manner, the whole of both side surfaces 214 (314) of the first storage portion 210 (310) is guided along the guide member 627 (first guide portion 627a) having the shape reflecting the shape of the first storage portion 210 (310), whereby the finger(s) of the user can be reliably prevented from entering the inner back side of each reagent container holding portion 62 from the space between the respective ones of the first storage portion 210 (310) and the guide member 627 when setting the reagent container 200 (300).

According to the first embodiment, as hereinabove described, each guide member 627 includes the first guide portion 627a guiding both side surfaces 214 (314) of the first storage portion 210 (310) and leading the first storage portion 210 (310) to the first acceptance portion 621 and the second guide portions 627c guiding the second storage portion 220 to the second acceptance portion 623. When forming the second measurement unit 2 (the first measurement unit 3) in this manner, the first storage portions 210 and 310 of the reagent containers 200 and 300 and the second storage portion 220 of the reagent container 200 are guided along the first guide portion 627a and the second guide portion 627c of the guide member 627 respectively, whereby the finger(s) of the user can avoid entering the inner back side of the reagent container holding portion 62 not only by the first guide portion 627a of the guide member 627 but also by the second guide portion 627c.

According to the first embodiment, as hereinabove described, each second storage portion 220 has the width W22 larger than the width W21 of the first storage portion 210, and the first guide portion 627a is provided in the width W11 smaller than the width W22 of the second storage portion 220. When forming the second measurement unit 2 (the first measurement unit 3) in this manner, the first storage portion 210 inserted into the inner back side of the reagent container holding portion 62 and the first guide portion 627a guiding the first storage portion 210 both have the widths smaller than that of the second storage portion 220 of the reagent container 200, whereby the finger(s) of the user hardly enters the inner back side of the reagent container holding portion 62. Thus, the finger(s) of the user can further reliably avoid touching the piercer 64 when setting each reagent container 200.

According to the first embodiment, as hereinabove described, each second storage portion 220 has the width W22 larger than the width W21 of the first storage portion 210, and the first guide portion 627a is provided in the width W11 smaller than the width W22 of the second storage portion 220. When forming the second measurement unit 2 (the first measurement unit 3) in this manner, the volume of the reagent storable in each reagent container can be enlarged also when the first guide portion 627a has such a width that the finger(s) of the user hardly enters the inner back side of the reagent container holding portion 62.

According to the first embodiment, as hereinabove described, each first acceptance portion 621 has the width W11 inhibiting entrance of the finger(s) of the user. When forming the second measurement unit 2 (the first measurement unit 3) in this manner, entrance of the finger(s) of the user into the first acceptance portion 621 accepting the first storage portion 210 (310) into which the piercer 64 enters, whereby the finger(s) of the user can reliably avoid touching the piercer 64 when setting each reagent container 200 (300).

According to the first embodiment, as hereinabove described, each reagent container holding portion 62 includes the support portion 624 supporting the reagent container 200 (300) and the rotation mechanism 625 moving the support portion 624 to the placed position P1 for placing the reagent container 200 (300) on the support portion 624 and the set position Q1 for arranging the reagent container 200 (300) on the support portion on a position where the piercer 64 is enterable. When forming the second measurement unit 2 (the first measurement unit 3) in this manner, the user can set each reagent container 200 (300) on the reagent container holding portion 624 by simply moving the support portion 624 to the set position Q1 with the rotation mechanism 625, whereby he/she can easily set the reagent container 200 (300) on the reagent container holding portion 62, while the user may not insert the finger(s) (hand) into the inner back side of the reagent container holding portion 62.

According to the first embodiment, as hereinabove described, each piercer raising/lowering mechanism 65 is formed to move the corresponding piercer 64 in association with opening/closing of the cover 63, and so formed that the piercer 64 retreats out of (to above) the first acceptance portion 621 when the cover 63 is arranged on the raised position P2 opening the reagent container holding portion 62. When forming the second measurement unit 2 (the first measurement unit 3) in this manner, the piercer 64 retreats out of the first storage portion 210 (310) when moving the cover 63 to the raised position P2 for setting the reagent container 200 (300), whereby the set operation for the reagent container 200 (300) can be simplified. Further, the finger(s) of the user can more reliably avoid touching the piercer 64 when setting the reagent container 200 (300).

According to the first embodiment, as hereinabove described, each cover 63 is formed to open and close the reagent container holding portion 62 in association with movement of the piercer 64 by the piercer raising/lowering mechanism 65. When forming the second measurement unit 2 (the first measurement unit 3) in this manner, movement of the piercer 64 by the piercer raising/lowering mechanism 65 can be interlocked with the cover 63 opening and closing the reagent container holding portion 62 itself. Thus, the piercer 64 retreats out of the reagent container 200 (300) when opening the cover 63 for setting the reagent container 200 (300), whereby the finger(s) of the user can more reliably avoid touching the piercer 64.

According to the first embodiment, as hereinabove described, the entrance portion 212 (312) of each reagent container 200 (300) is so provided that the piercer 64 of the first measurement unit 3 (second measurement unit 2) is enterable from above in the vicinity of the forward end in the direction inserted into the first measurement unit 3 (second measurement unit 2). Thus, the piercer 64 of the first measurement unit 3 (second measurement unit 2) can be advanced into the reagent container 200 (300) from above through the entrance portion 212 (312) inserted into the inner back side of the first measurement unit 3 (second measurement unit 2). Therefore, the user can set the reagent container 200 (300) by simply grasping the reagent container 200 (300) and inserting the same into the first measurement unit 3 (second measurement unit 2) from the side of the entrance portion 212 (312) on the forward end, whereby the set operation for the reagent container 200 (300) can be simplified. Further, the advancement of the piercer 64 into the reagent container 200 (300) and the retreat from the reagent container 200 (300) can be performed on the inner back side in the insertional direction in the first measurement unit 3 (second measurement unit 2), whereby the finger(s) of the user can avoid touching the piercer 64 when setting the reagent container 200 (300).

According to the first embodiment, as hereinabove described, the inner bottom surface 200a (300a) of each reagent container 200 (300a) is formed to be unparallel to the outer upper surface 200b (300b), while the reagent container 200 (300) is so formed that the distance between the inner bottom surface 200a (300a) and the outer upper surface 200b (300b) enlarges as approaching the entrance portion 212 (312). When forming the blood analysis system 1 in this manner, the position of the inner bottom surface 200a (300a) immediately under the entrance portions 212 (312) most lowers in the reagent container 200 (300) when setting the reagent container 200 (300) so that the outer upper surface 200b (300b) is horizontal. Thus, the quantity of the reagent not suckable by the piercer 64 but remaining in the reagent container 200 (300) can be reduced.

According to the first embodiment, as hereinabove described, the entrance portion 212 (312) of each reagent container 200 (300) is provided on an end portion of the first storage portion 210 (310) in the direction (arrow Y2 direction in FIGS. 7 and 8) where the first storage portion 210 (310) is inserted into the reagent container holding portion 62. When forming the reagent container 200 (300) in this manner, the entrance portion 212 (312) is arranged on the inner back of the first acceptance portion 621 in the case of setting the reagent container 200 (300) on the reagent container holding portion 62, whereby the piercer 64 can also be arranged on the inner back of the first acceptance portion 621 correspondingly to the position of the entrance portion 212 (312). Thus, the finger(s) of the user can more reliably avoid touching the piercer 64.

According to the first embodiment, as hereinabove described, the second storage portion 220 of each reagent container 200 is constituted of the first portion 222, continuous with the first storage portion 210, whose width enlarges as separating from the first storage portion 210 and the second portion 223, continuous with the first portion 222, having the constant width W22. When forming the reagent container 200 (300) in this manner, the reagent stored in the side of the second portion 223 is collected on the side of the entrance portion 212 through the first portion 222 in a case of arranging each reagent container 200 on the set position Q1 so that the position of the inner bottom surface 200a (bottom portion 200c) on the side of the entrance portion 212 lowers in the reagent container 200, whereby the reagent in the reagent container 200 does not remain on the side of the second storage portion 220.

According to the first embodiment, as hereinabove described, each piercer raising/lowering mechanism 65 is formed to move the piercer 64 in association with opening/closing of the cover 63. Introduction/withdrawal of the reagent container 200 (300) into/from the reagent container holding portion 62 is allowed when the cover 63 moves to the raised position P2 opening the reagent container holding portion 62, and introduction/withdrawal of the reagent container 200 (300) into/from the reagent container holding portion 62 is inhibited when the cover 63 moves to the lowered position Q2 closing the reagent container holding portion 62. When forming the second measurement unit 2 (the first measurement unit 3) in this manner, the user can retreat the piercer 64 out of the reagent container 200 (300) and can bring the reagent container 200 (300) into a state advanceable/withdrawable into/from the reagent container holding portion 62 by simply moving the cover 63 to the raised position P2. After setting the reagent container 200 (300) on the reagent container holding portion 62, the user can inhibit introduction/withdrawal of the reagent container 200 (300) into/from the reagent container holding portion 62 and can advance the piercer 64 into the reagent container 200 (300) by simply moving the cover 63 to the lowered position Q2. Consequently, the user can render the reagent suckable from inside the reagent container 200 (300) by performing the operations of the movement of the cover 63 to the raised position P2, the setting of the reagent container 200 (300) and the movement of the cover 63 to the lowered position Q2. Thus, the set operation for the reagent container 200 (300) can be simplified without complicating the device structure.

In the first embodiment, such a case is also conceivable that a stain solution is stored in any reagent container 200 (or 300) and the stain solution adheres to the piercer 64. Therefore, the stain solution can be prevented from adhering to the finger(s) of the user by forming the second measurement unit 2 (the first measurement unit 3) so that the finger(s) does not touch the piercer 64 as in the aforementioned first embodiment.

According to the first embodiment, each reagent container holder 60 includes the five holder portions 60a, 60b, 60c, 60d and 60e, and is formed to hold five (five types of) reagent containers 200 (or 300) in total. Thus, as compared with such a structure that one suction pipe sucks reagents from a large number of reagent containers, each piercer 64 corresponds to each reagent container 200 (300) and hence a carryover of the reagent can be prevented. In a case where the reagent is a stain solution, a smear of the piercer 64 is hard to remove even by washing, and hence this is particularly preferable.

According to the first embodiment, the color of each reagent container 200 (300) is black. Thus, the reagent in the reagent container 200 (300) can be prevented from deterioration resulting from external light. In a case where the reagent is a stain solution, deterioration resulting from light easily takes place, and hence this is particularly preferable.

Second Embodiment

A second embodiment of the present invention is now described with reference to FIGS. 1, 6 and 19 to 25. This second embodiment is formed to interlock both of a piercer raising/lowering mechanism 850 and a rotation mechanism 825 with opening/closing of each cover 830, dissimilarly to the aforementioned first embodiment formed to interlock each piercer raising/lowering mechanism 65 with opening/closing of each cover 63 and to manually move each support portion 624. Structures other than each reagent container holder 800 are similar to those of the aforementioned first embodiment, and hence description is omitted. In the second embodiment, an example of setting a reagent container 200 on the reagent container holder 800 is described, and description as to a case of setting a reagent container 300 is omitted.

Figure 19:
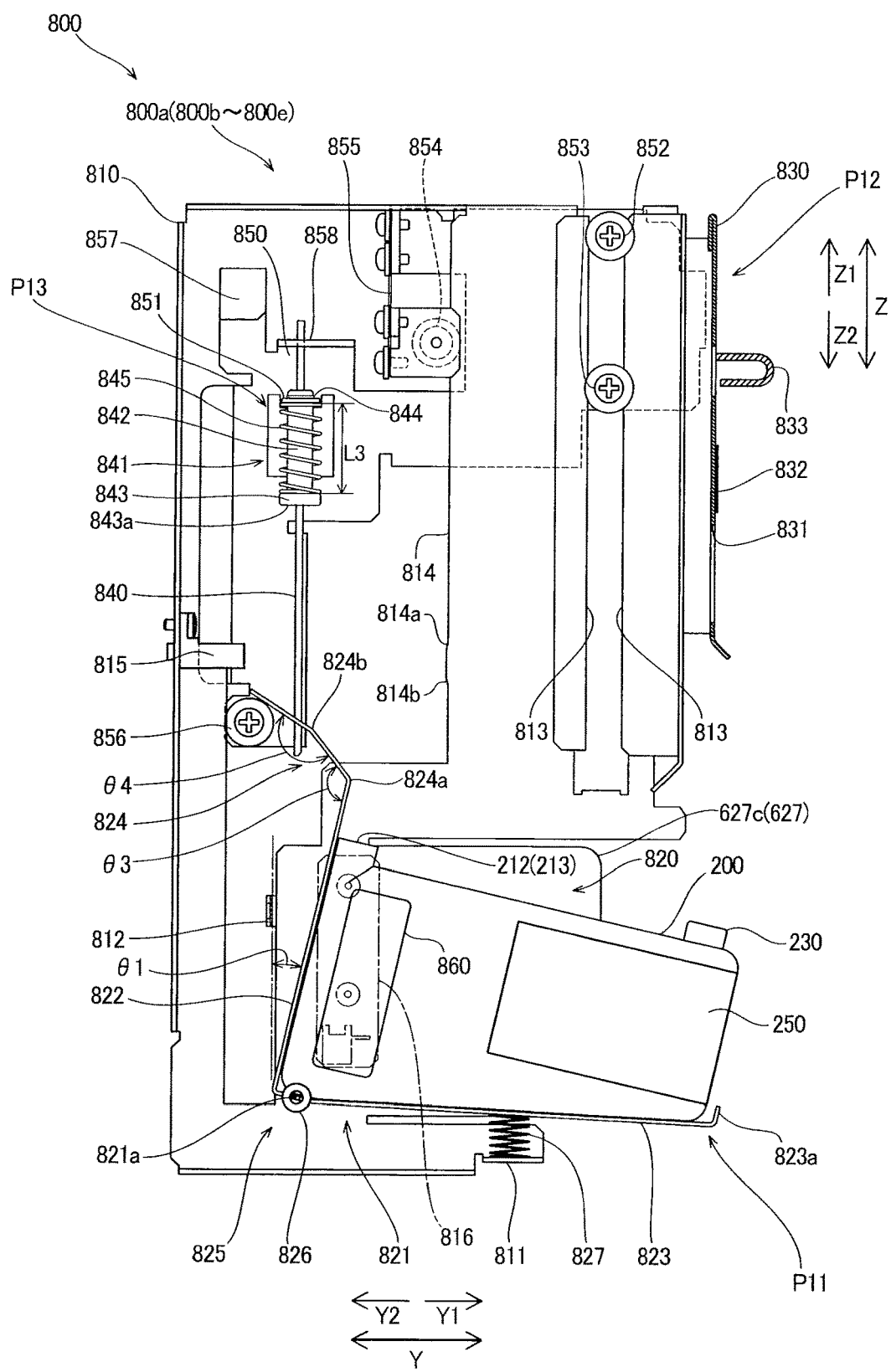
FIG. 19 is a longitudinal sectional view schematically showing a state where a cover of a reagent container holder of a second measurement unit according to a second embodiment of the present invention is opened.

According to the second embodiment, each of holder portions 800a to 800e of the reagent container holder 800 mainly includes a chassis 810, a reagent container holding portion 820, the cover 830 for opening/closing the reagent container holding portion 820, a piercer 840 and the piercer raising/lowering mechanism 850, as shown in FIG. 19.

The reagent container holding portion 820 includes a first acceptance portion 621, an intermediate acceptance portion 622 and a second acceptance portion 623 shown in FIG. 6. The structures of the first acceptance portion 621, the intermediate acceptance portion 622 and the second acceptance portion 623 are similar to those of the aforementioned first embodiment, and hence signs identical to those of the aforementioned first embodiment are employed while description is omitted. Similarly, the reagent container holding portion 820 includes a pair of guide members 627 guiding both side surfaces 214 (314) of a first storage portion 210 (310) of each reagent container 200 (300) and leading the same to the first acceptance portion 621. The pair of guide members 627 have first guide portions 627a guiding the first storage portion 210 (310) of the reagent container 200 (300) to the first acceptance portion 621, intermediate guide portions 627b corresponding to the intermediate acceptance portion 622 and second guide portions 627c guiding a second storage portion 220 (320) of the reagent container 200 (300) to the second acceptance portion 623 respectively. The structures of these guide members 627 (the first guide portions 627a, the intermediate guide portions 627b and the second guide portions 627c) are similar to those of the aforementioned first embodiment, and hence signs identical to those in the aforementioned first embodiment are employed and description is omitted.

As shown in FIG. 19, the reagent container holding portion 820 includes a support portion 821 supporting the reagent container 200 and a rotation mechanism 825 rotatably supporting the support portion 821. According to the second embodiment, the support portion 821 consists of a platelike member integrally having a front side portion 822 coming into contact with the front surface of the reagent container 200, a lower side portion 823 coming into contact with the lower surface of the reagent container 200, a contact portion 824, and a rear side portion 823a. The front side portion 822 and the lower side portion 823 of the support portion 821 are formed to have shapes corresponding to the shape of the reagent container 200. The rear side portion 823a is a portion where the platelike member (support portion 821) is bent upward on the rear end of the lower side portion 823. It becomes easy to set the reagent container 200 on a constant position on the support portion 821 (lower side portion 823), due to this rear side portion 823a.

The contact portion 824 of the support portion 821 is a site provided to extend from the upper end of the front side portion 822, and bent on bent portions 824a and 824b of two places. The contact portion 824 has a function of limiting or allowing movement of the support portion 821 from a placed position P11 to a set position Q11 (see FIG. 20) by coming into contact with a roller 856 described later. Further, the contact portion 824 is formed to jackknife at an angle θ3 on the bent portion 824a, and to jackknife at an angle θ4 larger than the angle θ3 on the bent portion 824b. A portion of the contact portion 824 between the bent portion 824a and the bent portion 824b and a portion on a forward end side (arrow Y2 direction side) beyond the bent portion 824b are linearly (planarly) formed.

The rotation mechanism 825 is so formed that a protrusion 821a provided on the support portion 821 is inserted into an annular bearing 826 provided on an inner side surface of the chassis 810 to be capable of rotating the support portion 821 on the position, serving as a rotation center, of the protrusion 821a (bearing 826). According to the second embodiment, the rotation mechanism 825 has a spring member 827 urging the support portion 821 to move to the set position Q11. The spring member 827 consists of a helical compression spring, and is so formed that a lower end is fixed onto a spring set portion 811 provided on a lower portion of the chassis 810 while an upper end comes into contact with the lower surface of the lower side portion 823 of the support portion 821. The spring member 827 is provided to enter a compressed state in a state where the support portion 821 is arranged on the placed position P11. The lower side portion 823 is pushed up due to repulsion (urging force) of this spring member 827, whereby the support portion 821 is urged to move (rotate) to the set position Q11.

Figure 20:
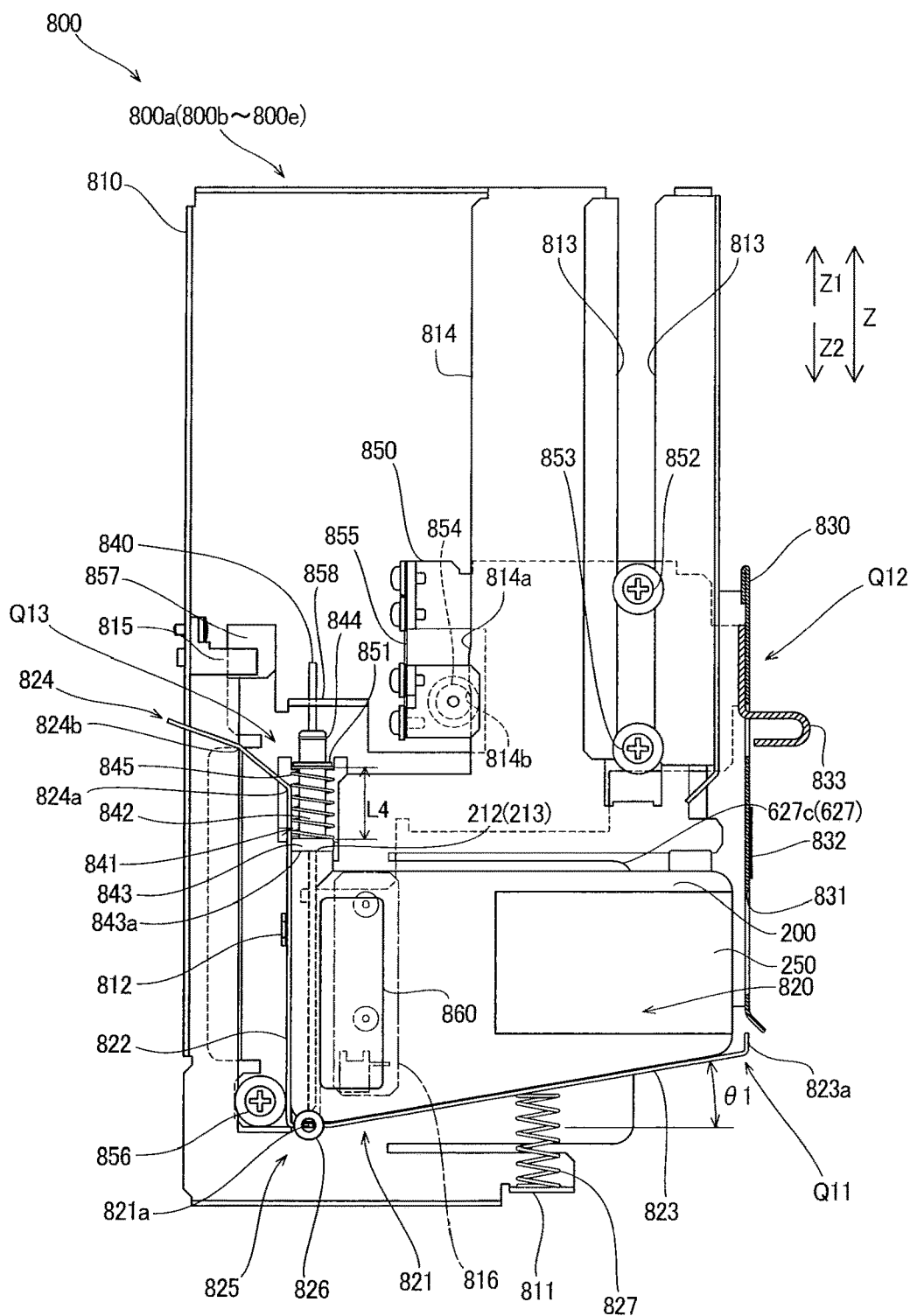
FIG. 20 is a longitudinal sectional view schematically showing a state where the cover of the reagent container holder of the second measurement unit according to the second embodiment of the present invention is closed.

As shown in FIG. 19, the second embodiment is so formed that movement of the support portion 821 by the rotation mechanism 825 is performed in association with opening/closing (movement to a raised position P12 and a lowered position Q12 (see FIG. 20)) of the cover 830. In other words, the contact portion 824 and the roller 856 of the piercer raising/lowering mechanism 850 come into contact with each other and movement of the contact portion 824 is limited in a case where the cover 830 is opened (a case where the same is positioned on the raised position P12), whereby movement of the support portion 821 to the set position Q11 by the rotation mechanism 825 is limited. In a case where the cover 830 is closed (a case where the same is positioned on the lowered position Q12) as shown in FIG. 20, on the other hand, the contact between the contact portion 824 and the roller 856 is canceled, whereby movement of the support portion 821 to the set position Q11 is allowed.

Figure 23:
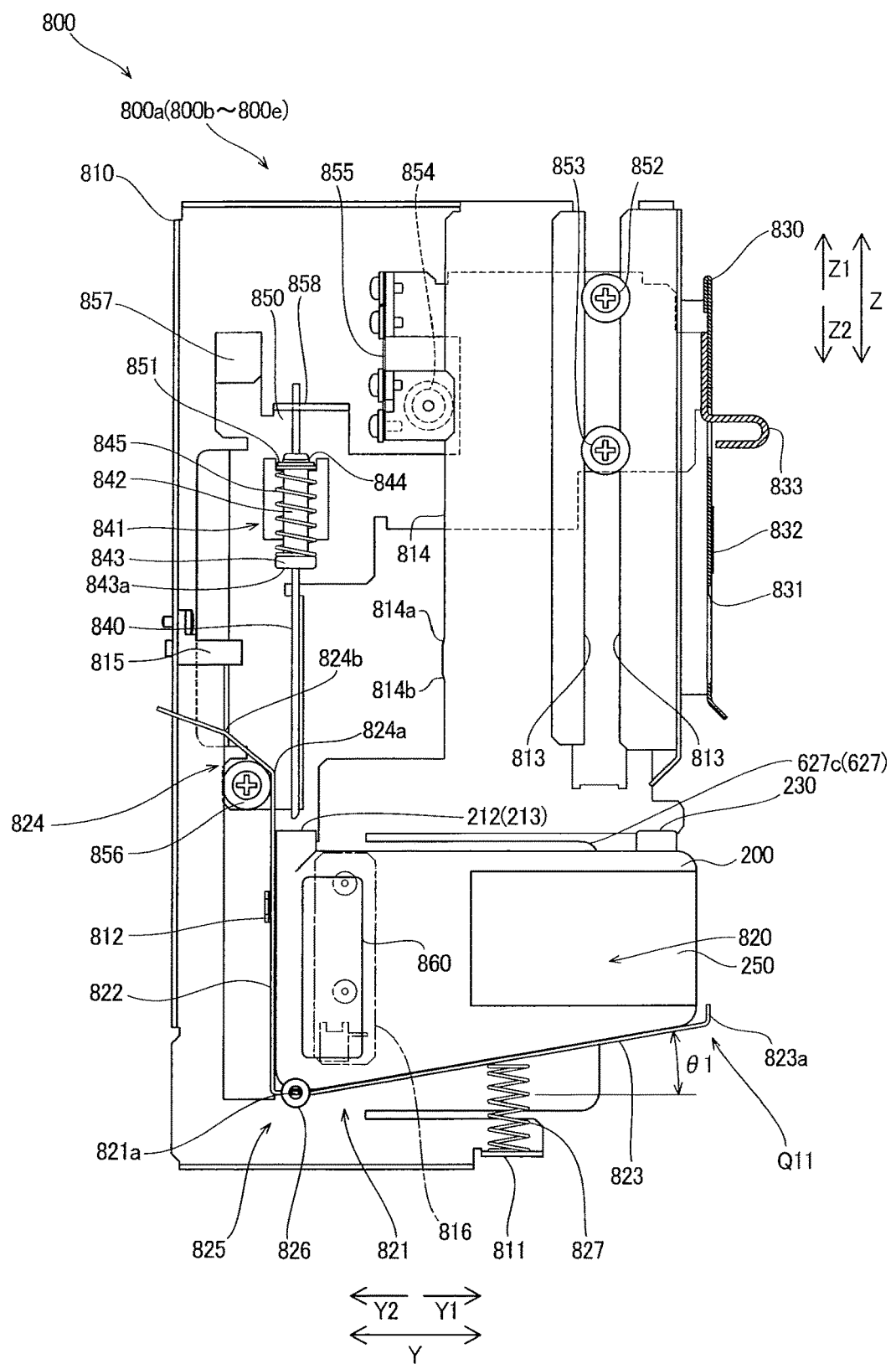
FIG. 23 is a diagram for illustrating a state where a support portion of the reagent container holder is arranged on a set position in the sectional view of FIG. 19.

A locking portion 812 locking the rotating portion 821 by coming into contact with the front side portion 822 of the support portion 821 is provided in the chassis 810. In a state where movement of the support portion 821 to the set position?Q11 is allowed (a case where the cover 830 is located on the lowered position Q12), therefore, the front side portion 822 is pressed against the locking portion 812 due to the urging force of the spring member 827, so that the support portion 821 is held on the set position Q11. In a case where the cover 830 lowers from the raised position P12 as shown in FIG. 23, therefore, the support portion 821 is arranged on the set position Q11 at a point of time when the roller 856 of the piercer raising/lowering mechanism 850 passes through the bent portion 824a before the cover 830 reaches the lowered position Q12. At the point of time when the support portion 821 is arranged on the set position Q11, the piercer 840 is arranged on a position immediately in front of (in the vicinity of) an entrance portion 212 of the reagent container 200 set on the support portion 821.

The cover 830 is mounted on the piercer raising/lowering mechanism 850, and formed to be movable to the raised position P12 opening the reagent container holding portion 820 and the lowered position Q12 (see FIG. 20) covering (closing) the reagent container holding portion 820 with this piercer raising/lowering mechanism 850, as shown in FIG. 19. The cover 830 is formed to allow introduction/withdrawal of the reagent container 200 (300) on the raised position P12 and to inhibit introduction/withdrawal of the reagent container 200 (300) on the lowered position Q12. As shown in FIG. 20, the cover 830 is so formed that the user can visually recognize a label 250 stuck to the reagent container 200 through a window portion 831 in a state where the cover 830 is located on the lowered position Q12. A label 832, on which an indicator for identifying the type of the reagent container 200 (the type of the reagent) set on the reagent container holding portion 820 is printed, is stuck to the cover 830.

According to the second embodiment, a cover grasp portion 833 is provided to protrude frontward (arrow Y1 direction) on a front surface side (arrow Y1 direction side) of the cover 830. Thus, it becomes possible for the user to perform opening/closing (movement to the raised position P12 or the lowered position Q12) of the cover 830 by grasping the cover grasp portion 833.

As shown in FIGS. 6 and 19, the piercer 840 is arranged on a position above the innermost portion (arrow Y2 direction side) of the first acceptance portion 821 of the reagent container holding portion 820, and formed to be moved in the vertical direction (direction Z) by the piercer raising/lowering mechanism 850. Thus, the piercer 840 enters the first storage portion 210 (310) through an entrance portion 212 (312) of the reagent container 200 (300) inserted into an inner back side of the reagent container holding portion 820, and is formed to be capable of sucking the reagent in the reagent container 200 (300). According to the second embodiment, the piercer 840 is held in a state fixed to an axial center (see FIG. 22) of a cylindrical piercer holding portion 841.

The piercer holding portion 841 integrally includes a columnar shaft portion 842 and a flange portion 843 formed to spread the outer diameter on a lower end of the shaft portion 842. The piercer holding portion 841 is so formed that the entrance portion 212 of the reagent container 200 and a lower surface 843a of the piercer holding portion 841 (flange portion 843) come into contact with each other to stop advancement of the piercer 840 into the regent container 200 when the piercer 840 enters the reagent container 200 through the entrance portion 212 (opening 212a). Thus, the piercer 840 is arranged on a lowered position Q13. At this time, the entrance portion 212 of the reagent container 200 and the lower surface 843a of the piercer holding portion 841 (flange portion 843) come into contact with each other, whereby the opening 212a is lidded.

Figure 21:
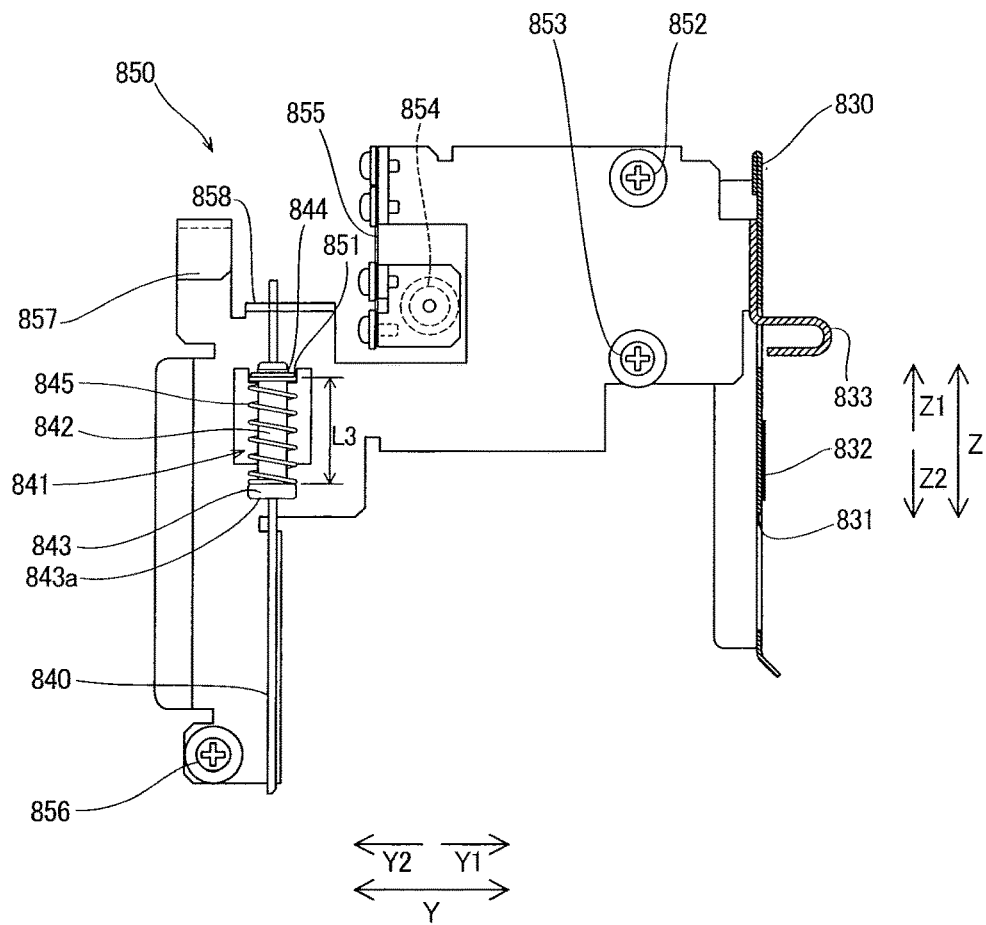
FIG. 21 is a side elevational view showing a piercer raising/lowering mechanism of the reagent container holder of the second measurement unit according to the second embodiment of the present invention.
Figure 22:
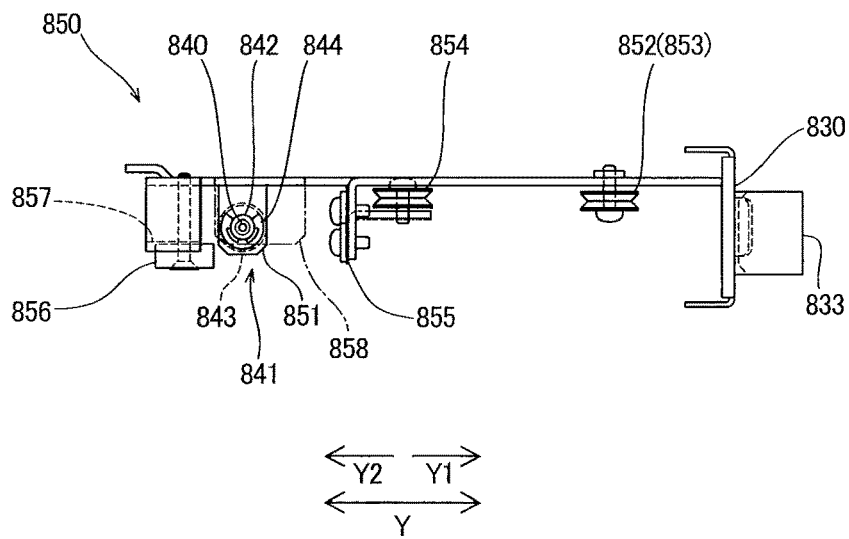
FIG. 22 is a plan view observing the piercer raising/lowering mechanism of FIG. 21 from above.

As shown in FIGS. 21 and 22, an upper end portion of the shaft portion 842 protruding upward (arrow Z1 direction) from a mounting portion 851 of the piercer raising/lowering mechanism 850 is locked by a stopper 844 (see FIG. 22), whereby the piercer holding portion 841 is mounted on the mounting portion 851 to be suspended. Thus, the piercer holding portion 841 is formed to be relatively movable in an upper direction (Z1 direction) where the piercer 840 retreats from the reagent container 200 with respect to the mounting portion 851 of the piercer raising/lowering mechanism 850.

A spring member 845 consisting of a helical compression spring is provided on the outer periphery of the shaft portion 842 of the piercer holding portion 841. The spring member 845 is so provided that the lower end comes into contact with the upper surface of the flange portion 843 and the upper end comes into contact with the lower surface of the mounting portion 851 of the piercer raising/lowering mechanism 850. Therefore, the spring member 845 is formed to urge the piercer holding portion 841 in a lower direction (Z2 direction) where the piercer 840 enters the reagent container 200 with respect to the mounting portion 851 of the piercer raising/lowering mechanism 850. As shown in FIG. 19, the spring member 845 has a spring length L3 in an uncompressed state.

As shown in FIGS. 21 and 22, the piercer raising/lowering mechanism 850 is formed to hold the cover 830 and to hold the piercer 840 through the piercer holding portion 841 mounted on the mounting portion 851. As shown in FIG. 19, the piercer raising/lowering mechanism 850 includes three guide rollers 852, 853 and 854 each having a V-shaped groove (see FIG. 22). The guide rollers 852 and 853 engage with a guide portion 813 on a front side (arrow Y1 direction side) of the chassis 810 in a vertically movable manner. The guide roller 854 engages with a guide portion 814 on an inner back side (arrow Y2 direction side) of the chassis 810 in a vertically movable manner. Thus, the piercer raising/lowering mechanism 850 is formed to integrally move the piercer 840 in the vertical direction (direction Z) in association with opening/closing (raising/lowering) of the cover 830.

The guide roller 854 is mounted on the piercer raising/lowering mechanism 850 through a plate spring 855, and engages with the guide portion 814 in a state urged frontward (arrow Y1 direction side) by the plate spring 855. A projectional portion having a first inclining portion 814a and a second inclining portion 814b is formed on a lower portion of the guide portion 814. The guide roller 854 urged frontward (arrow Y1 direction side) through the plate spring 855 moves to get over the first inclining portion 814a at the time of lowering. In a case where the user closes the cover 830, therefore, the user feels resistance when the guide roller 854 gets over the first inclining portion 814a and is capable of reliably recognizing that he/she has pushed down the cover 830 up to the lowered position Q12. On the other hand, the guide roller 854 must get over the second inclining portion 814b in order to raise the cover 830, and hence the second inclining portion 814b has a function of fixing the position of the cover 830 (piercer raising/lowering mechanism 850) to the lowered position Q12 in a case where the cover 830 is arranged on the lowered position Q12.

Figure 25:
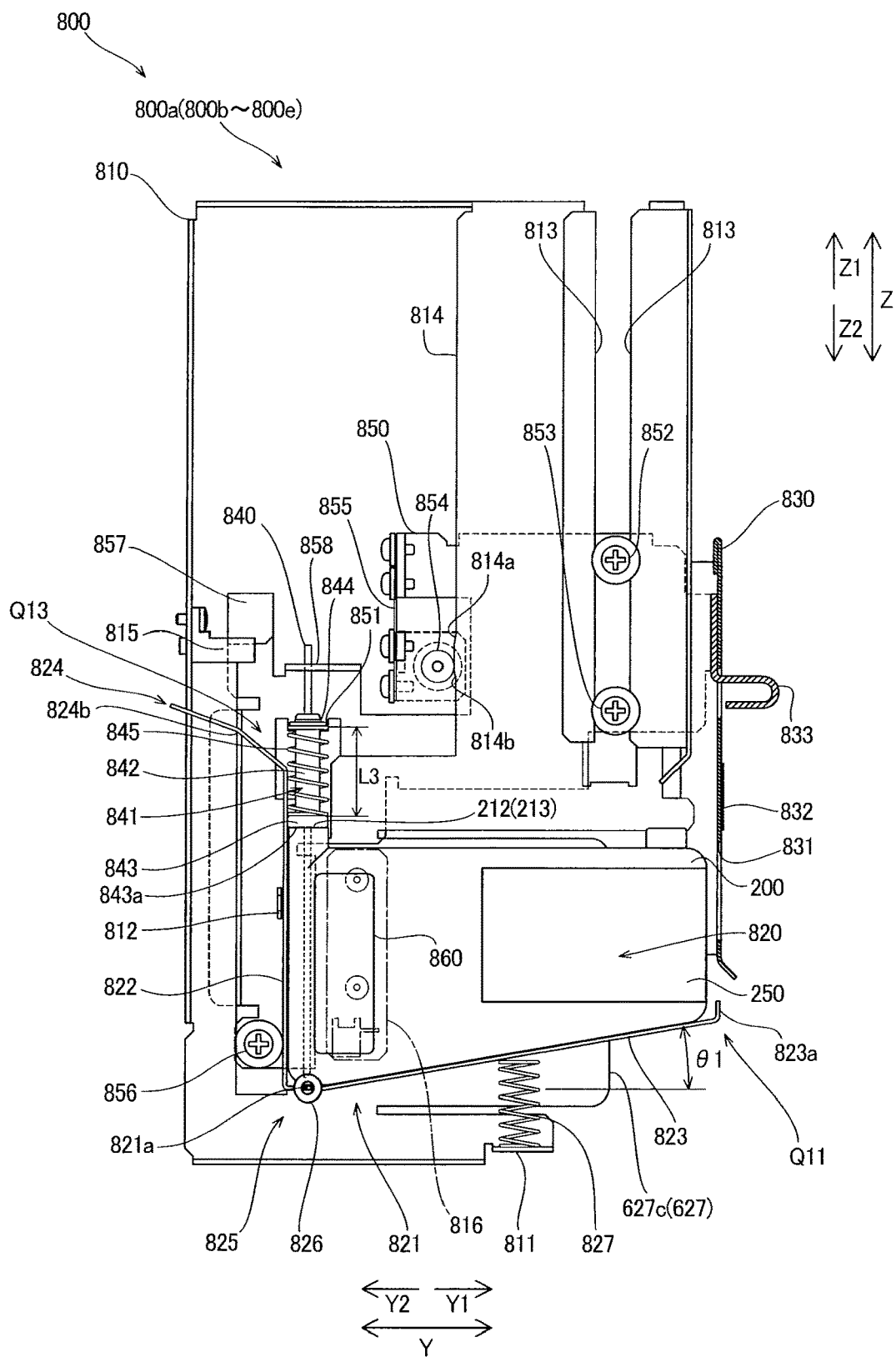
FIG. 25 is a diagram for illustrating a state where the piercer of the reagent container holder is arranged on a lowered position in the sectional view of FIG. 19.

As shown in FIG. 25, the entrance portion 212 of the reagent container 200 and the lower surface 843a of the flange portion 843 of the piercer holding portion 841 come into contact with each other before the cover 830 reaches the lowered position Q12, and the piercer 840 is arranged on the lowered position Q13. From the time when the piercer 840 has been arranged on the lowered position Q13 up to the time when the cover 830 reaches the lowered position Q12 (see FIG. 20), therefore, the mounting portion 851 lowers following the lowering of the cover 830 (piercer raising/lowering mechanism 850), thereby operating to compress the spring member 845 of the piercer holding portion 841. Therefore, the spring member 845 of the piercer holding portion 841 is compressed to a spring length L4 in the state where the cover 830 is arranged on the lowered position Q12. Thus, the piercer holding portion 841 is so formed that the spring member 845 presses the guide roller 854 of the piercer raising/lowering mechanism 850 against the second inclining portion 814b through the mounting portion 851 and the spring member 845 presses the piercer holding portion 841 against the reagent container 200 through the flange portion 843. The piercer holding portion 841 is so formed in this manner that the piercer holding portion 841 and the reagent container 200 can be reliably brought into contact with each other due to repulsion of the spring member 845 of the piercer holding portion 841 even if the lowered position Q12 (position of the second inclining portion 814b) for the cover 830 slightly deviates upward or downward due to a production error or the like, thereby preventing the position of the piercer 840 with respect to the reagent container 200 from dispersing every holder portion (800a to 800e).

According to the second embodiment, the roller 856 vertically moving integrally with the piercer raising/lowering mechanism 850 (cover 830) is provided on a lower portion of an inner back side (arrow Y2 direction side) of the piercer raising/lowering mechanism 850. In a case where the cover 830 is located on the raised position P12, the roller 856 comes into contact with the contact portion 824 of the support portion 821, as shown in FIG. 19. Thus, the roller 856 is formed to limit movement of the contact portion 824 (support portion 821) urged by the spring member 827 to move to the set position Q11. In a case where the cover 830 is located on the lowered position Q12, the roller 856 is formed to allow the support portion 821 to move to the set position Q11, as shown in FIG. 20. Thus, the second embodiment is so formed that both of movement of the piercer 840 by the piercer raising/lowering mechanism 850 and movement of the support portion 821 by the rotation mechanism 825 (spring member 827) are parallelly performed in association with opening/closing (raising/lowering) of the cover 830.

A detection fragment 857 is provided on an upper portion of the inner back side (arrow Y2 direction side) of the piercer raising/lowering mechanism 850. This detection fragment 857 is formed to detect that the cover 830 has been arranged on the lowered position Q12 (the piercer 840 has been arranged on the lowered position Q13) by blocking an optical sensor (photointerrupter) 815 provided on the chassis 810, as shown in FIG. 20. A piercer regulation portion 858 so provided that the piercer 840 passes through an opening is arranged above the mounting portion 851. The piercer regulation portion 858 has a function of inhibiting the piercer 840 (piercer holding portion 841) from moving to rotate on the mounting portion 851. FIG. 22 illustrates the piercer regulation portion 858 with one-dot chain lines.

An RFID (Radio Frequency Identification) antenna portion 816 (see one-dot chain lines) for performing near field communication is provided on a position in the vicinity of the first acceptance portion 621 outside the chassis 810. According to the second embodiment, an RFID tag 860 is stuck to an outer side surface of the first storage portion 210 of the reagent container 200. Reagent information such as the type, the lot number, the expiration date etc. of the reagent stored in the reagent container 200, for example, is recorded on this RFID tag 860. The RFID tag 860 is so formed that, when the reagent container 200 is set on the support portion 821, the RFID tag 860 of the reagent container 200 and the RFID antenna portion 816 (see the one-dot chain lines) perform near field communication so that the reagent information is read. The read reagent information is acquired by a control device 5 (see FIG. 1), and an error message is displayed on a display portion 52 (see FIG. 1) in a case where an erroneous reagent (reagent container 200) is set or the like.

A set operation for the reagent container 200 onto the reagent container holder 800 (holder portion 800*a*) of each of a first measurement unit 3 and a second measurement unit 2 (see FIG. 1) according to the second embodiment is now described with reference to FIGS. 1, 6 and 19 to 25. The set operation is similar in the reagent containers 200 and 300, and hence only the set operation for the reagent container 200 is described, and the set operation for the reagent container 300 is omitted. Similarly, only the set operation for the reagent container 200 onto the holder portion 800*a* is described, and description is omitted as to set operations onto the remaining holder portions 800*b* to 800*e*.

First, the user opens a front surface cover 24*a* (see FIG. 1), and moves the cover 830 to the raised position P12 (see FIG. 19) (opens the cover 830) by grasping the cover grasp portion 833. At this time, the piercer 840 and the roller 856 of the piercer raising/lowering mechanism 850 move upward following upward movement of the cover 830 and the roller 856 comes into contact with the contact portion 824 on the bent portion 824*a*, as shown in FIG. 23. At this time, the piercer 840 retreats out of (upwardly from) the reagent container 200. The support portion 821 having the contact portion 824 is urged by the spring member 827, and hence the roller 856 rises to push the contact portion 824 aside toward the arrow Y1 direction side. Thus, at the same time when the piercer 840 rises toward the raised position P13 in association with the raising of the cover 830, the support portion 821 is parallelly rotated toward the arrow Y1 direction side and starts moving to the placed position P11.

Figure 24:
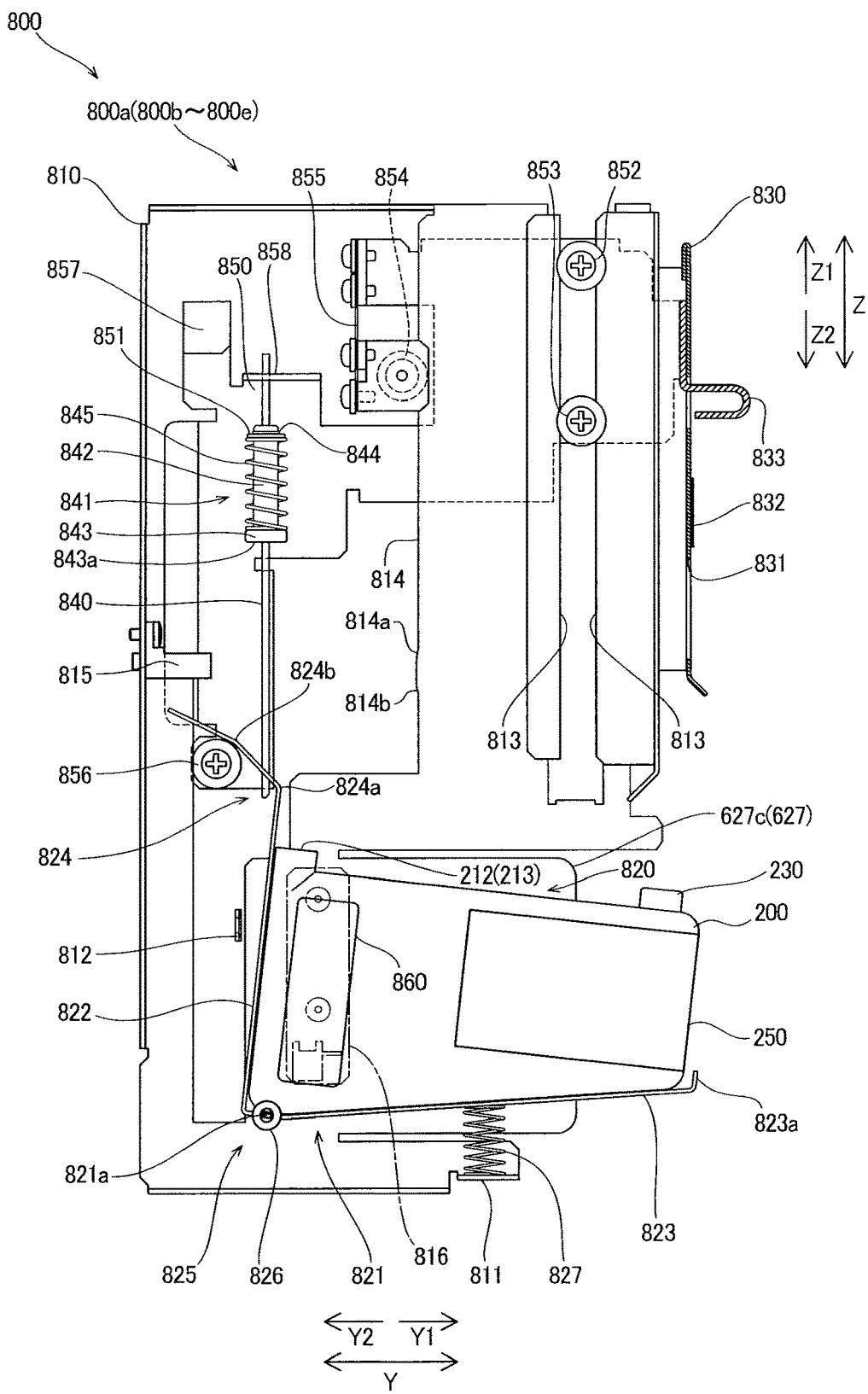
FIG. 24 is a diagram for illustrating an opening/closing operation for the cover of the reagent container holder in the sectional view of FIG. 19.

When continuing the raising of the cover 830, the roller 856 comes into contact with the contact portion 824 on the bent portion 824*b*, as shown in FIG. 24. The angle θ4 of the bent portion 824*b* is larger than the angle θ3 of the bent portion 824*a*, and hence movement (rotation angle) of the support portion 821 following the raising of the cover 830 increases while upthrust force necessary for raising the cover 830 (roller 856) increases following this bent portion 824*b*. Thus, it is possible to suppress abrupt increase of upthrust force (i.e. resistance received by the user) necessary when the user pushes up the cover 830 by providing the bent portions 824*a* and 824*b* on the two places and reducing the angle in the bent portion 824*a* (angle θ3) below the bent portion 824*b* (angle θ4). Further, movement of the overall cover 830 (roller 856) necessary for increasing the movement (rotation angle) of the support portion 821 and moving (rotating) the support portion 821 to the set position Q11 and the placed position P11 can be inhibited from increasing by enlarging the angle on the bent portion 824*b* (angle θ4), whereby it is possible to inhibit the reagent container holder 800 from size increase.

When continuing the raising past the bent portion 824*b*, the cover 830 is arranged on the raised position P12 and the reagent container holding portion 820 is opened while the piercer 840 is arranged on the raised position P13, as shown in FIG. 19. Further, the roller 856 of the piercer raising/lowering mechanism 850 comes into contact with a forward end portion of the contact portion 824, whereby rotation of the support portion 821 toward the arrow Y2 direction side with the spring member 827 is limited, and the support portion 821 is held on the placed position P11.

Then, the user places the reagent container 200 on the support portion 821 (exchanges an old reagent container 200 for a new reagent container 200). At this time, the reagent information recorded on the RFID tag 860 stuck to the reagent container 200 is read by the control device 5 (see FIG. 1) through the RFID antenna portion 816 (see the one-dot chain lines) set outside the chassis 810. In a case where an erroneous reagent (reagent container 200) is set, an error message is displayed on the display portion 52 (see FIG. 1), and it is posted to the user that this is an erroneous reagent.

The shapes of the first acceptance portion 621 and the guide members 627 (see FIG. 6) are similar to those of the aforementioned first embodiment, and hence the whole of both side surfaces 214 of the first storage portion 210 is guided by a pair of first guide portions 627*a* reflecting the shape of the first storage portion 210 also in the second embodiment, whereby the finger(s) of the user is prevented from entering an inner back side of the reagent container holding portion 62 from a space between the reagent container 200 (respective side surfaces of the first storage portion 210 and the second storage portion 220) and the guide members 627 (first guide portions 627*a* and second guide portions 627*c*) in insertion of the reagent container 200. Thus, the finger(s) of the user is prevented from touching the piercer 840.

Then, the user grasps the cover grasp portion 833 and moves (lowers) the cover 830 from the raised position P12 to the lowered position Q12 (see FIG. 20) (closes the cover 830), as shown in FIG. 19. The piercer 840 and the roller 856 of the piercer raising/lowering mechanism 850 lower following this. The support portion 821 is urged toward the arrow Y2 direction side by the spring member 827, whereby the support portion 821 gradually rotates toward the arrow Y2 direction side following the lowering of the roller 856 in the state where the roller 856 and the contact portion 824 are in contact with each other. When the roller 856 lowers up to the bent portion 824*a* as shown in FIG. 23, the front side portion 822 of the support portion 821 comes into contact with the locking portion 812. Thus, the support portion 821 is arranged on the set position Q11, while the rotation of the support portion 821 is stopped by the locking portion 812. At this time, the piercer 840 is arranged on a position (position immediately in front of the entrance portion 212 (opening 212a)) above the entrance portion 212 (opening 212a) of the reagent container 200 and in the vicinity of the entrance portion 212 (opening 212a). When the support portion 821 is arranged on the set position Q11, the front side portion 822 comes into contact with the locking portion 812 and is locked, whereby only the piercer 840 moves following the lowering of the cover 830 after the roller 856 passes through the bent portion 824a.

When the user continuously lowers the cover 830, the piercer 840 passes through a sealing member 213 sealing the entrance portion 212 (opening 212a) of the reagent container 200 and enters the reagent container 200 through the entrance portion 212 (opening 212a). While the cover 830 reaches the lowered position Q12, the guide roller 854 of the piercer raising/lowering mechanism 850 gets over the first inclining portion 814a. The user feels resistance when the guide roller 854 gets over the first inclining portion 814a and can reliably recognize that he/she has pushed down the cover 830 up to a prescribed position.

As shown in FIG. 25, the lower surface of the piercer holding portion 841 and the upper end surface of the entrance portion 212 of the reagent container 200 come into contact with each other in a state where the guide roller 854 is positioned between the first inclining portion 814a and the second inclining portion 814b, and the lowering of the piercer 840 stops. Therefore, the piercer 840 is arranged on the lowered position Q13 at this point of time. After the piercer 840 is arranged on the lowered position Q13, the piercer holding portion 841 moves relatively upward (direction where the piercer 840 retreats) with respect to the piercer raising/lowering mechanism 850 when the cover 830 (piercer raising/lowering mechanism 850) further lowers. In other words, the piercer holding portion 841 holds the position thereof to protrude upward from the mounting portion 851 with respect to the lowering of the cover 830 (piercer raising/lowering mechanism 850). After the piercer 840 is arranged on the lowered position Q13, therefore, only the cover 830 (piercer raising/lowering mechanism 850) lowers while the support portion 821 and the piercer 840 stop.

When the guide roller 854 passes through the second inclining portion 814b, the spring member 845 of the piercer holding portion 841 is compressed following the lowering of the piercer raising/lowering mechanism 850 (mounting portion 851). Urging force acts on the piercer raising/lowering mechanism 850 upward (arrow Z1 direction) due to repulsion of this spring member 845, whereby the guide roller 854 stops on a position meshing with the second inclining portion 814b. Thus, the cover 830 is held on the lowered position Q12 in the state where the spring member 845 is compressed up to the spring length L4, as shown in FIG. 20. At this time, the detection fragment 857 of the piercer raising/lowering mechanism 850 blocks the sensor 815, and it is detected that the cover 830 has been closed (has been arranged on the lowered position Q12). On the basis of this detection result, it becomes possible to suck the reagent in the reagent container 200 through the piercer 840.

In this state, it becomes possible for the user to visually recognize the label 250 of the reagent container 200 from the window portion 831 of the cover 830, whereby it becomes possible for the user to confirm from the label 832 stuck to the cover 830 and the label 250 of the reagent container 200 whether or not a correct reagent container 200 is set and what reagent (reagent container 200) provided with which label 250 may be prepared in exchange of the reagent.

Thus, the set operation for the reagent container 200 onto the reagent container holder 800 (holder portion 800a) terminates.

According to the second embodiment, as hereinabove described, the rotation mechanism 825 is formed to move the support portion 821 in association with movement of the cover 830 so that the support portion 821 is located on the placed position P11 when moving the cover 830 to the raised position P12 and the support portion 821 is located on the set position Q11 when moving the cover 830 to the lowered position Q12. The rotation mechanism 825 is so formed in this manner that movement of the cover 830 and movement of the support portion 821 interlock with each other, whereby the user can arrange the reagent container 200 on the set position Q11 where the piercer 840 is enterable by simply moving the cover 830 to the lowered position Q12 after setting the reagent container 200 on the support portion 821. Thus, setting or withdrawal of the reagent container 200 can be easily performed without complicating the device structure. Further, the user may not touch the reagent container 200 in order to arrange the reagent container 200 on the set position Q11 where the piercer 840 is enterable, whereby the finger(s) of the user can more reliably avoid touching the piercer 840.

According to the second embodiment, as hereinabove described, the spring member 827 urging the support portion 821 to move to the set position Q11 is provided, whereby the support portion 821 can be easily moved from the placed position P11 to the set position Q11.

According to the second embodiment, as hereinabove described, the contact portion 824 and the roller 856 are so provided that the support portion 821 can be prevented from being erroneously moved, whereby the finger(s) of the user can more reliably avoid touching the piercer 840.

According to the second embodiment, as hereinabove described, the roller 856 moving in association with opening/closing of the cover 830 and the contact portion 824 moving in association with movement of the support portion 821 are provided and the roller 856 and the contact portion 824 so come into contact with each other that movement of the contact portion 824 is limited and allowed, whereby movement of the support portion 821 from the placed position P11 to the set position Q11 is limited and allowed. Thus, limitation and allowance of movement of the support portion 821 from the placed position P11 to the set position Q11 can be easily interlocked with opening/closing of the cover 830 by employing the roller 856 and the contact portion 824.

According to the second embodiment, as hereinabove described, the cover grasp portion 833 is provided on the front surface side (arrow Y1 direction side) of the cover 830, whereby the user can move the cover 830 by holding the cover grasp portion 833 arranged on the front surface side of the cover 830. Thus, the finger(s) of the user can more reliably avoid touching the piercer 840, while movement of the cover 830 can be easily performed.

According to the second embodiment, as hereinabove described, the piercer raising/lowering mechanism 850 is formed to move the piercer 840 in association with movement (opening/closing) of the cover 830 while both of movement of the piercer 840 with the piercer raising/lowering mechanism 850 and movement of the support portion 821 with the rotation mechanism 825 are parallelly performed in association with movement (opening/closing) of the cover 830. When forming the piercer raising/lowering mechanism 850 in this manner, the user can perform movement of the support portion 821 from the placed position P11 to the set position Q11 and advancement of the piercer 840 into the reagent container 200 (movement of the piercer 840 from the raised position P13 to the lowered position Q13) by simply closing the cover 830 after moving the cover 830 to the raised position P12 and setting the reagent container 200 on the support portion 821. In a case of moving the piercer 840 after moving the support portion 821 in association with movement of the cover 830, for example, the distance of movement of the cover 830 from the raised position P12 to the lowered position Q12 must be enlarged, and hence the device is increased in size. On the other hand, the piercer raising/lowering mechanism 850 is so formed that both of movement of the piercer 840 and movement of the support portion 821 are parallelly performed in association with movement (opening/closing) of the cover 830 so that the distance of movement of the cover 830 from the raised position P12 to the lowered position Q12 can be reduced, whereby the device can be inhibited from size increase.

According to the second embodiment, as hereinabove described, the piercer holding portion 841 is formed to stop advancement of the piercer 840 into the reagent container 200 by coming into contact with the entrance portion 212 of the reagent container 200 when the piercer 840 enters the reagent container 200 through the entrance portion 212. Further, the piercer holding portion 841 is formed to be relatively movable in an upper direction (arrow Z1 direction) retreating the piercer 840 out of the reagent container 200 with respect to the piercer raising/lowering mechanism 850 (mounting portion 851) following movement of the piercer raising/lowering mechanism 850 to the side of the reagent container 200 after coming into contact with the entrance portion 212 of the reagent container 200. When forming the piercer holding portion 841 in this manner, the piercer holding portion 841 relatively moves with respect to the piercer raising/lowering mechanism 850 in the state where the piercer holding portion 841 is in contact with the upper end surface of the entrance portion 212 of the reagent container 200 also in a case of moving the piercer raising/lowering mechanism 850 in a direction (arrow Z2 direction) for further advancing the piercer 840 after the piercer holding portion 841 comes into contact with the upper end surface of the entrance portion 212 of the reagent container 200. Therefore, the piercer 840 can be prevented from further entering the reagent container 200. Thus, the forward end of the piercer 840 can be regularly arranged on a constant position in the reagent container 200 without separately providing a sensor or the like in order to perform positioning of the piercer raising/lowering mechanism 850.

According to the second embodiment, as hereinabove described, the spring member 845 urging the piercer holding portion 841 in the lower direction (arrow Z2 direction) for advancing the piercer 840 into the reagent container 200 with respect to the piercer raising/lowering mechanism 850 (mounting portion 851) is provided. When forming the spring member 845 in this manner, the spring member 845 urges the piercer holding portion 841 in the lower direction (arrow Z2 direction) for advancing the piercer 840. Therefore, the contact state between the piercer holding portion 841 and the upper end surface of the entrance portion 212 can be maintained due to the urging force of the spring member 845 also in a case where the piercer raising/lowering mechanism 850 moves in the direction (arrow Z2 direction) where the piercer 840 enters after the piercer holding portion 841 comes into contact with the upper end surface of the entrance portion 212 of the reagent container 200. Thus, the forward end of the piercer 840 can be reliably held on the constant position in the reagent container 200 with the spring member 845.

According to the second embodiment, as hereinabove described, the cover 830 is formed to open the reagent container holding portion 820 on the raised position p12 allowing withdrawal of the reagent container 200 and to close the reagent container holding portion 820 on the lowered position Q12 preventing withdrawal of the reagent container 200 from the reagent container holding portion 820. When forming the cover 830 in this manner, movement of the piercer 840 with the piercer raising/lowering mechanism 850 can be interlocked with the cover 830 opening and closing the reagent container holding portion 820. Thus, the reagent can be rendered settable (or exchangeable) by retreating the piercer 840 out of the reagent container 200 when opening the cover 830 for setting the reagent container 200, and the piercer 840 can be advanced into the reagent container 200 by simply closing the cover 830 after setting the reagent container 200. Consequently, the user can render the reagent suckable from inside the reagent container 200 by simply closing the cover 830 after opening the cover 830 and setting the reagent container 200, whereby the set operation for the reagent container 200 can be simplified.

According to the second embodiment, as hereinabove described, the entrance portion 212 of the reagent container 200 and the lower surface 843a of the piercer holding portion 841 (flange portion 834) come into contact with each other, whereby the opening 212a is lidded. Thus, in such an analysis device that the reagent container 200 is kept being set until next reagent exchange in a state where the piercer 840 lowers once the reagent container 200 is set, drying of the reagent or contamination with foreign matter can be prevented in a simple structure.

The remaining effects of the second embodiment are similar to those of the aforementioned first embodiment.

Third Embodiment

A third embodiment of the present invention is now described with reference to FIGS. 17, 19 and 26 to 28. In this third embodiment, dedicated reagent container holding portions 920 and 930 are provided for large-sized reagent containers 200 and small-sized reagent containers 300 respectively, dissimilarly to each of the aforementioned first and second embodiments so formed that the large-sized reagent containers 200 and the small-sized reagent containers 300 are held by the common reagent container holding portions 62 (820). As to a structure other than the reagent container holding portions 920 and 930, either the structure of the aforementioned first embodiment or the structure of the aforementioned second embodiment may be employed, and hence description is omitted.

Figure 26:
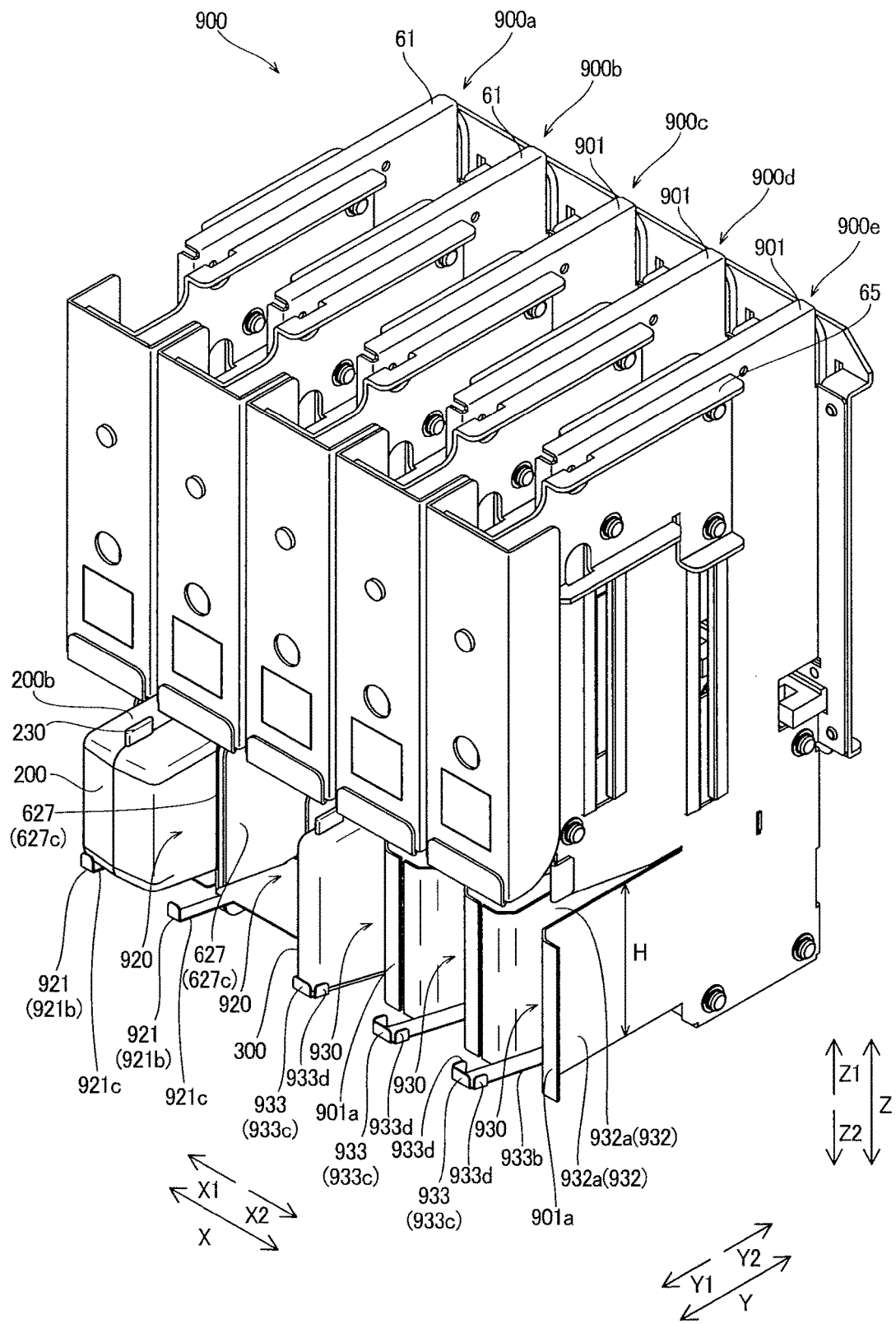
FIG. 26 is a perspective view for illustrating a reagent container holding portion of a reagent container holder of a second measurement unit according to a third embodiment of the present invention.

As shown in FIG. 26, a reagent container holder 900 includes two holder portions 900a and 90b provided with the reagent container holding portions 920 dedicated to the large-sized reagent containers 200 and three holder portions 900c, 900d and 900e provided with the reagent container holding portions 930 dedicated to the small-sized reagent containers 300 in the third embodiment.

Figure 27:
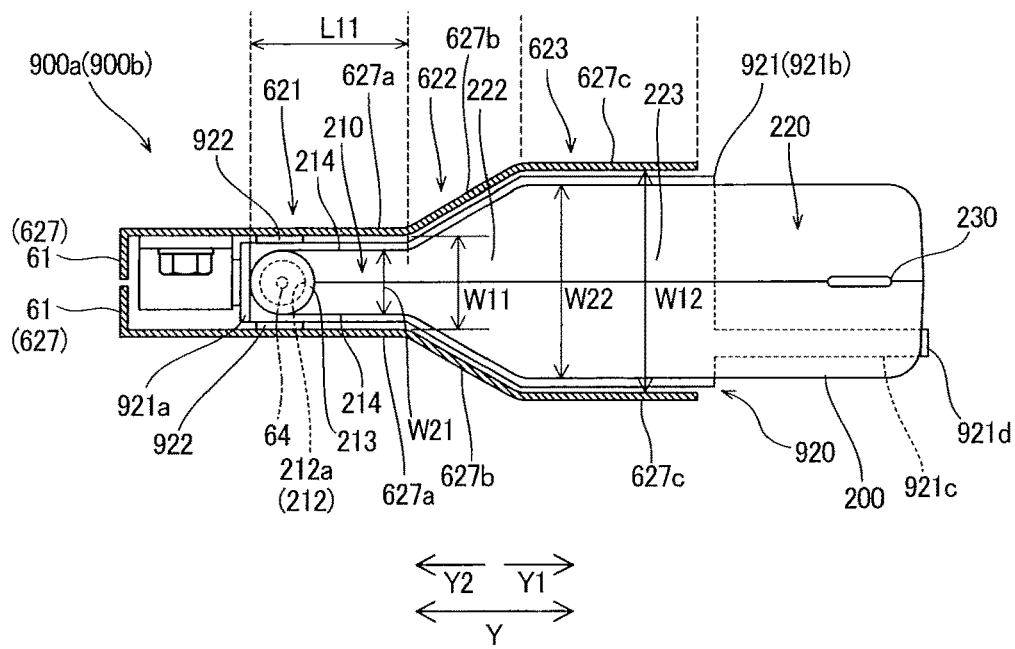
FIG. 27 is a schematic diagram showing a reagent container holding portion, for a large-sized reagent container, of the reagent container holder shown in FIG. 26.

As shown in FIGS. 26 and 27, each reagent container holding portion 920 dedicated to each of the large-sized reagent containers 200 has a height H, and includes a first acceptance portion 621 having a width W11, an intermediate acceptance portion 622 and a second acceptance portion 623, similarly to each reagent container holding portion 62 (820) according to each of the aforementioned first and second embodiments. Similarly, the reagent container holding portion 920 includes a pair of guide members 627 guiding both side surfaces 214 of a first storage portion 210 of each reagent container 200 and leading the same to the first acceptance portion 621. The guide members 627 have first guide portions 627a, intermediate guide portions 627b and second guide portions 627c. The pair of guide members 627 (the first acceptance portion 621, the intermediate acceptance portion 622 and the second acceptance portion 623) have shapes reflecting the outer shape of the reagent container 200 respectively, and are formed to be capable of guiding the whole of both side surfaces 214 of the first storage portion 210 of the reagent container 200 and both side surfaces of a forward end-side (arrow Y2 direction) half of the second storage portion 220.

As shown in FIG. 27, the reagent container holding portion 920 includes a support portion 921 supporting the reagent container 200 and a rotation mechanism 922 rotatably supporting the support portion 921. The support portion 921 is a platelike member integrally having a front side portion 921a coming into contact with a front surface of the reagent container 200 (forward end surface of the first storage portion 210), a lower side portion 921b coming into contact with the lower surface of the reagent container 200, an extensional portion 921c extending from the lower side portion 921b toward a front side (rear end side of the second storage portion 220, an arrow Y1 direction) and a rear end portion 921d provided on an end portion of the extensional portion 921c. The support portion 921 may be provided with a contact portion similarly to the support portion 821 (see FIG. 19) of the aforementioned second embodiment, and may be so formed that the contact portion and a roller come into contact with each other so that movement of the support portion 921 is limited or allowed.

As shown in FIG. 26, the extensional portion 921c extending from the lower side portion 921b is formed on a position deviating toward one side (arrow X1 direction side) in the width direction of the support portion 921, and formed to linearly extend in the arrow Y1 direction. The rear end portion 921d is a portion where the platelike member (support portion 921) is bent upward on the forward end (end portion on the arrow Y1 direction side) of the extensional portion 921c. As shown in FIG. 27, the length of the extensional portion 921c in a direction Y corresponds to the length of the reagent container 200 in the longitudinal direction, and the support portion 921 is so formed that the rear end portion 921d functions as a positioning portion for the reagent container 200 when setting the reagent container 200 on the support portion 921. Thus, it becomes easy for the user to set the reagent container 200 on a constant position on the support portion 921 (lower side portion 921b). In a case where the user grasps the rear end portion (second storage portion 220) of the reagent container 200 to hold the same in the vertical direction when setting the reagent container 200, the extensional portion 921c is arranged to deviate to one side (arrow X1 direction side) of the support portion 921 and hence the extensional portion 921c and the rear end portion 921d do not hinder the setting of the reagent container 200.

The remaining structure of the reagent container holding portion 920 is similar to that of the reagent container holding portion 62 in the aforementioned first embodiment or the reagent container holding portion 820 in the second embodiment, and hence description is omitted.

Figure 28:
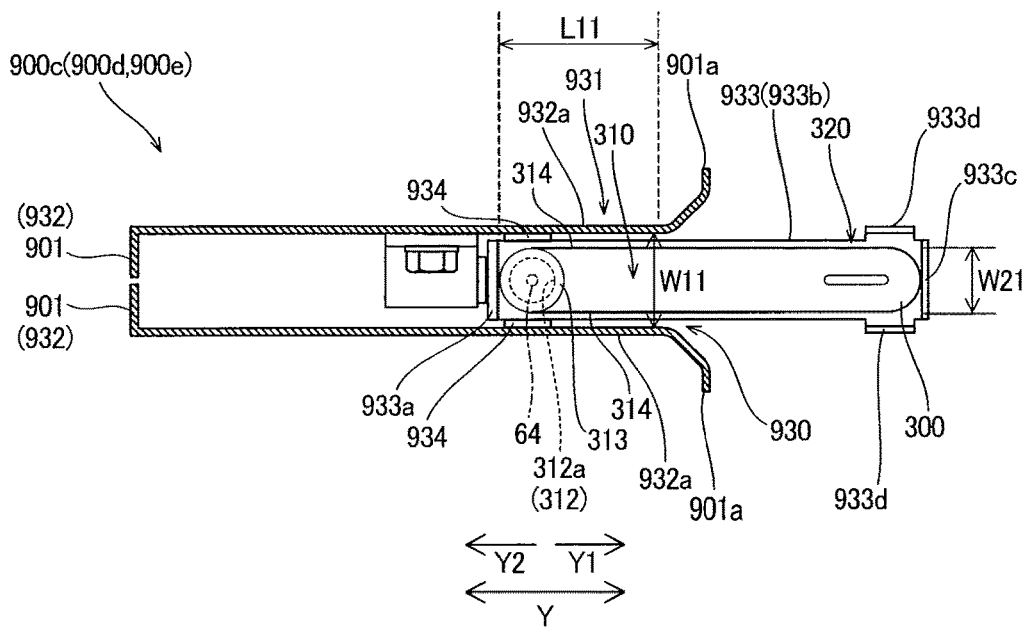
FIG. 28 is a schematic diagram showing a reagent container holding portion, for a small-sized reagent container, of the reagent container holder shown in FIG. 26.

As shown in FIGS. 26 and 28, each reagent container holding portion 930 dedicated to each of the small-sized reagent containers 300 has the height H, and includes a first acceptance portion 931 having the width W11. The first acceptance portion 931 is capable of accepting a first storage portion 310 of each reagent container 300, and has the width (width W11, 10 mm, for example) inhibiting entrance of the finger(s) of the user. The first acceptance portion 931 is arranged on the innermost side (arrow Y2 direction side) of the reagent container holding portion 930, and the reagent container 300 is inserted from the side of an entrance portion 312 of the first storage portion 310 toward an inner back side of the reagent container holding portion 930. Therefore, the reagent container holding portion 930 is formed to hold the reagent container 300 in a state so inserted that the entrance portion 312 of the reagent container 300 is on the innermost side.

Further, the reagent container holding portion 930 includes a pair of guide members 932 guiding both side surfaces 314 of the first storage portion 310 of the reagent container 300 and leading the same to the first acceptance portion 931. The pair of guide members 932 have first guide portions 932a guiding the first storage portion 310 of the reagent container 300 to the first acceptance portion 931 respectively. The pair of guide members 932 are formed by parts (both inner side surfaces) of a chassis 901 of the holder portion 900c (900d and 900e) provided with the reagent container holding portion 930, and the aforementioned first acceptance portion 931 is formed by a space between the pair of first guide portions 932a. A bent portion 901a spreading outside in the width direction (direction X) of the reagent container holding portion 930 is formed on a front-side (arrow Y1 direction-side) end portion of the guide member 932 (chassis 901).

As shown in FIGS. 26 and 28, the pair of guide members 932 have the height H substantially equal to a height H1 (see FIG. 17) of both side surfaces 314 of the first storage portion 310 of the reagent container 300 respectively, and are formed to be capable of guiding both side surfaces 314 of the first storage portion 310 of the reagent container 300 from lower ends up to upper ends. Further, the pair of guide members 932 have planar shapes reflecting the outer shape of the first storage portion 310 respectively, and are formed to be capable of guiding the whole of both side surfaces 314 of the first storage portion 310 of the reagent container 300. Therefore, the width W11 of the first acceptance portion 931 is equal to the width of the space between the first guide portions 932a.

As shown in FIG. 28, the reagent container holding portion 930 includes a support portion 933 supporting the reagent container 300 and a rotation mechanism 934 rotatably supporting the support portion 933. The support portion 933 is a platelike member integrally having a front side portion 933a coming into contact with the front surface of the reagent container 300 (forward end surface of the first storage portion 310), a lower side portion 933b coming into contact with the lower surface of the reagent container 300, a rear end portion 933c provided on an end portion on a front side of the lower side portion 933b (rear end side of the second storage portion 320, an arrow Y1 direction) and a pair of upright portions 933d provided on both side portions of a front-side end portion of the lower side portion 933b. The support portion 933 may be provided with a contact portion similarly to the support portion 821 (see FIG. 19) of the aforementioned second embodiment, and may be so formed that the contact portion and a roller come into contact with each other and movement of the support portion 933 is limited or allowed.

As shown in FIG. 26, the rear end portion 933c is a portion where the platelike member (support portion 933) is bent upward on the forward end of the lower side portion 933*b* (end portion on the arrow Y1 direction side). The length of the lower side portion 933*b* in the direction Y corresponds to the length of the reagent container 300 in the longitudinal direction, and the support portion 933 is so formed that the rear end portion 933*c* functions as a positioning portion for the reagent container 300 when setting the reagent container 300 on the support portion 933. Thus, it becomes easy for the user to set the reagent container 300 on a constant position on the support portion 933 (lower side portion 933*b*).

The pair of upright portions 933*d* are portions where the platelike member (support portion 933) is bent upward on both side portions of the front-side end portion of the lower side portion 933*b*. As shown in FIG. 28, the interval between the pair of upright portions 933*d* is substantially equal to the interval (width W11 of the first acceptance portion 931) between the pair of guide members 932 (first guide portions 932*a*), and the pair of upright portions 933*d* are formed to be capable of supporting both side surfaces of a rear end portion of the second storage portion 320 of the reagent container 300. In other words, the width W21 of the second storage portion 320 is small as compared with the width W22 of the second storage portion 220 of the first reagent container 200, and hence the small-sized reagent container 300 is inferior in stability in the lateral direction (direction X) to the large-sized reagent container 200. Therefore, it is possible to stably hold the reagent container 300 in the reagent container holding portion 930 by supporting both side surfaces 314 of the first storage portion 310 of the reagent container 300 with the pair of guide members 932 (first guide portions 932*a*) and supporting the side of the second storage portion 320 of the reagent container 300 with the pair of upright portions 933*d*.

As shown in FIG. 26, the bent portion 901*a* spreading outside is formed on the front-side (arrow Y1 direction-side) end portion of the guide member 932 (chassis 901) in the reagent container holding portion 930, and hence the interval (interval in the direction X) to an adjacent reagent container holding portion 930 (reagent container 300) is large dissimilarly to the wide reagent container holding portion 920 where adjacent reagent container holding portions 920 approach each other. Therefore, the rear end portion 933*c* and the upright portions 933*d* do not hinder setting of the reagent container 300 when the user sets the reagent container 300 by grasping the rear end portion (second storage portion 320) of the reagent container 300 to hold the same in the horizontal direction in setting of the reagent container 300.

According to the third embodiment, as hereinabove described, the reagent container holding portions 920 dedicated to the large-sized reagent containers 200 and the reagent container holding portions 930 dedicated to the small-sized reagent containers 300 are provided, and the reagent container holding portions 920 and the reagent container holding portions 930 have the shapes reflecting the shapes of the reagent containers 200 and the reagent containers 300 respectively. Thus, it is possible to attain simplification of setting of the reagent containers 200 and the reagent containers 300 whose shapes are different from each other and to stably hold the reagent containers 200 and the reagent containers 300 on the reagent container holding portions 920 and 930 respectively.

The embodiments disclosed this time must be considered as illustrative in all points and not restrictive. The range of the present invention is shown not by the above description of the embodiments but by the scope of claims for patent, and all modifications within the meaning and range equivalent to the scope of claims for patent are further included.

For example, while the example of providing the two measurement units of the first measurement unit and the second measurement unit has been shown as an example of the analysis device in each of the aforementioned first to third embodiments, the present invention is not restricted to this. The number of measurement units may be one or at least three.

While the blood analysis system including the two measurement units, the sample transport device and the control device has been shown in each of the aforementioned first to third embodiments, the present invention is not restricted to this. The present invention may be applied to a simple measurement unit without constituting the aforementioned analysis system.

While the example of providing the five reagent container holding portions on each reagent container holder has been shown in each of the aforementioned first to third embodiments, the present invention is not restricted to this. One to four reagent container holding portions may be provided, or at least six reagent container holding portions may be provided. The reagent container holding portions may be provided by a number responsive to the types or the like of the reagents used in the analysis device.

While the example of forming the piercer raising/lowering mechanism 65 to move (raise/lower) the piercer 64 and the cover 63 in association with each other has been shown in the aforementioned first embodiment, the present invention is not restricted to this. The piercer raising/lowering mechanism may simply move the piercer inside and outside the reagent container without interlocking the same with the cover.

While the example of forming the piercer raising/lowering mechanism 850 to interlock both of movement (raising/lowering) of the piercer 840 with the piercer raising/lowering mechanism 850 and movement of the support portion 821 with the rotation mechanism 825 with opening/closing (raising/lowering) of the cover 830 has been shown in the aforementioned second embodiment, the present invention is not restricted to this. The present invention may be formed to interlock either one of movement (raising/lowering) of the piercer 840 and movement of the support portion 821 with opening/closing (raising/lowering) of the cover 830. For example, the present invention may be formed to interlock movement of the support portion with the rotation mechanism (support portion moving mechanism) and opening/closing of the cover and not to interlock movement of the piercer with the piercer raising/lowering mechanism with opening/closing of the cover. At this time, movement of the piercer with the piercer raising/lowering mechanism may become possible only in a state where the cover is closed (state where the support portion is arranged on the set position).

While the example of providing the cover 63 (830) for opening/closing the reagent container holding portion 62 (820) on each of the holder portions 60*a* (800*a*) to 60*e* (800*e*) has been shown in each of the aforementioned first and second embodiments, the present invention is not restricted to this. According to the present invention, a withdrawal prevention member that moves to a withdrawal position opening the reagent container holding portion and to a withdrawal prevention position partially covering the reagent container holding portion and inhibiting introduction/withdrawal of the reagent container may be provided without completely closing (covering) the reagent container holding portion. Therefore, the withdrawal prevention member may be a palisade member or a columnar member capable of partially covering the reagent container holding portion, or may be an engaging member allowing or inhibiting introduction/withdrawal of the reagent container by engaging with the reagent container without covering the reagent container holding portion, for example. Further, the withdrawal prevention member may be formed to collectively open/close a plurality of reagent container holding portions with one cover.

While the example of providing the pair of guide members on the reagent container holding portion 62 (820, 830 and 930) has been shown in each of the aforementioned first to third embodiments, the present invention is not restricted to this. According to the present invention, a single guide member guiding both side surfaces of the first storage portion of the reagent container may be provided without providing the pair of guide members. Further, guide members may be constituted of at least three members.

While the example of forming the guide members for the reagent container holding portion by parts (both inner side surfaces) of the chassis has been shown in each of the aforementioned first to third embodiments, the present invention is not restricted to this. According to the present invention, guide members may be provided as members separate from the chassis.

While the example of forming the reagent container 200 (300) so that the inner bottom surface 200a (300a) is unparallel to the outer upper surface 200b (300b) has been shown in the aforementioned first embodiment, the present invention is not restricted to this. According to the present invention, the inner bottom surface and the outer upper surface of the reagent container may be formed to be parallel to each other. Further, the inclining surface 200d (300d) may not be provided on the outer bottom surface of the reagent container 200 (300). In other words, the outer bottom surface and the outer upper surface of the reagent container may be formed to be parallel to each other, while the inner bottom surface of the reagent container may be formed to be unparallel to the outer upper surface of the reagent container (so that only the inner surface inclines).

While the example of forming the second storage portion 220 of the reagent container 200 by the first portion 222 whose width enlarges as separating from the first storage portion 210 and the second portion 223 having the constant width W22 has been shown in the aforementioned first embodiment, the present invention is not restricted to this. According to the present invention, the second storage portion may be formed only by the first portion, and may be so formed that the width continuously enlarges up to the rear end portion as separating from the first storage portion.

While the example of employing two types of reagent containers of the large-sized reagent container 200 having the volume of about 100 mL and the small-sized reagent container 300 having the volume of about 20 mL has been shown in the aforementioned first embodiment, the present invention is not restricted to this. According to the present invention, the reagent container(s) may be only one type, or may be at least three types. Further, the volumes of the reagent containers are not restricted to 100 mL and 20 mL either, but may be set to volumes responsive to the quantities of used reagents, frequencies etc.

While the example of forming the contact portion 824 to be bent on the two places of the bent portion 824a and the bent portion 824b has been shown in the aforementioned second embodiment, the present invention is not restricted to this. According to the present invention, the contact portion may have a smooth curved shape. Further, the contact portion may be provided with bent portion(s) on one place or at least three places.

While the example of integrally forming the contact portion 824 to extend from the upper end of the front side portion 822 of the support portion 821 has been shown in the aforementioned second embodiment, the present invention is not restricted to this. According to the present invention, the contact portion may be provided as a body different from the support portion (front side portion). In this case, the present invention may be so formed that the contact portion moves in association with the support portion also in the case where the contact portion is provided as the body different from the support portion.

While the example of forming the contact portion 824 and the roller 856 to limit and allow movement of the support portion 821 from the placed position P11 to the set position Q11 in association with opening/closing of the cover 830 has been shown in the aforementioned second embodiment, the present invention is not restricted to this. According to the present invention, a limitation portion other than the contact portion and the roller may be provided.

While such an example that the spring member 827 consisting of the helical compression spring is provided and the support portion 821 is urged to move to the set position Q11 has been shown in the aforementioned second embodiment, the present invention is not restricted to this. For example, a helical torsion coil spring (torsion spring) or a plate spring may be provided, so that the support portion 821 is urged by the same to move to the set position Q11.

While such an example that the spring member 845 urging the piercer holding portion 841 in the lower direction (Z2 direction) where the piercer 840 enters the reagent container 200 is provided has been shown in the aforementioned second embodiment, the present invention is not restricted to this. According to the present invention, the spring member 845 may not be provided.

While such an example that the piercer holding portion 841 holding the piercer 840 is provided has been shown in the aforementioned second embodiment, the present invention is not restricted to this. According to the present invention, the piercer holding portion 841 may not be provided, but the piercer 840 may be directly fixed to the mounting portion 851 of the piercer raising/lowering mechanism 850.

While the example of setting 10 mm as the width W11 which is such a width that the finger(s) of the user hardly enters has been shown in each of the aforementioned first to third embodiments, the present invention is not restricted to this. The width W11 may simply be about 5 mm to 20 mm, and is preferably 8 mm to 18 mm.

While the example of providing the guide members guiding both side surfaces of the first storage portion on the reagent container holding portion has been shown in each of the aforementioned first to third embodiments, the present invention is not restricted to this. According to the present invention, no guide members may be provided. Further, the guide members may be formed to guide only one side surface of the first storage portion, and the guide members may be formed to guide portions other than the first storage portion of the reagent container.

While such an example that the guide members 627 (932) have the shapes reflecting at least the shape of the first storage portion 210 (310) of the reagent container 200 (300) has been shown in each of the aforementioned first to third embodiments, the present invention is not restricted to this. According to the present invention, the guide members may not reflect the shape of the first storage portion of the reagent container. Therefore, the guide members may be formed to guide only parts of both side surfaces of the first storage portion without guiding the whole of both side surfaces of the first storage portion of the reagent container.

While such an example that the guide members 627 (932) are provided with the height H substantially equal to the height H1 of the first storage portion 210 (310) of the reagent container 200 (300) has been shown in each of the aforementioned first to third embodiments, the present invention is not restricted to this. According to the present invention, the guide members may be provided with a height dimension different from the height of the first storage portion of the reagent container. Therefore, the guide members may be formed to guide only central portions (central portions in the height direction) of both side surfaces of the first storage portion, for example, without guiding both side surfaces of the first storage portion from the upper ends up to the lower ends.

While the present invention has been applied to the hemocytometer performing flow cytometry in each of the aforementioned first to third embodiments, the present invention is not restricted to this. According to the present invention, it may be a urine particle analyzer performing flow cytometry. Such an analysis device performing flow cytometry classifies/counts particles by employing a stain solution staining cells such as red blood cells.

While it has been assumed that the color of the reagent container is black in each of the aforementioned first to third embodiments, the present invention is not restricted to this. According to the present invention, external advancement of light into the reagent container may simply be prevented. For example, the color of the reagent container may be brown. Further, the reagent container may be surface-treated with a material transmitting no light, in order to prevent external advancement of light into the reagent container.

What is claimed is:

1. An analysis device comprising:
    a reagent container holding portion configured to hold a reagent container inside, wherein the reagent container holding portion comprises an entrance through which the reagent container is insertable into and removable from the reagent container holding portion;
    a suction pipe adapted to aspirate a reagent from the reagent container held by the reagent container holding portion;
    a suction pipe moving mechanism operable to advance the suction pipe into the reagent container held by the reagent container holding portion and retreat the suction pipe out of the reagent container; and
    a cover adapted to move between a withdrawal position where the cover is positioned to uncover the entrance of the reagent container holding portion to enable the reagent container to be inserted into or removed from the reagent container holding portion through the entrance and a withdrawal prevention position where the cover is positioned to cover the entrance of the reagent container holding portion to prevent the reagent container inside the reagent container holding portion from being removed from the reagent container holding portion,
    wherein the cover is operably connected to the suction pipe moving mechanism so that a movement of the cover from the withdrawal position to the withdrawal prevention position will cause the suction pipe moving mechanism to move, along with the suction pipe, towards the reagent container and advance the suction pipe into the regent container, and a movement of the cover from the withdrawal prevention position to the withdrawal position will cause the suction pipe moving mechanism to retreat the suction pipe out of the reagent container and move, along with the suction pipe, away from the reagent container.

2. The analysis device according to claim 1, wherein the reagent container holding portion further includes a support portion configured to support the reagent container placed thereon and a support portion moving mechanism operable to move the support portion between a first position where the support portion is situated so that the reagent container is insertable into and removable from the reagent container holding portion through the entrance and a second position where the support portion is situated to position the reagent container on the support portion so that the suction pipe is enterable into the reagent container.

3. The analysis device according to claim 2, wherein the cover is operably connected to the support portion moving mechanism so that a movement of the cover from the withdrawal position to the withdrawal prevention position will cause the support portion moving mechanism to move the support portion from the first position to the second position, and a movement of the cover from the withdrawal prevention position to the withdrawal position will cause the support portion moving mechanism to move the support portion from the second position to the first position.

4. The analysis device according to claim 3, wherein the support portion moving mechanism includes a first urging member operable to urge the support portion towards the second position.

5. The analysis device according to claim 4, wherein the support portion moving mechanism includes a stopper mechanism operable to hold the support portion at the first position against an urging force of the first urging member.

6. The analysis device according to claim 5, wherein the stopper mechanism comprises a roller and an extension arm, the roller being operably connected to the suction pipe moving mechanism so that the roller will move along with a movement of the suction pipe, and the extension arm being operably connected to the support portion so that the extension arm will move along with a movement of the support portion, and
    the extension arm comprises a distal end shaped to engage with the roller to hold the support member at the first position against an urging force of the first urging member when the cover is at the withdrawal position.

7. The analysis device according to claim 6, wherein the roller is operably connected to the suction pipe moving mechanism so that when the cover starts to move from the withdrawal position towards the withdrawal prevention position, the roller will move along with the cover to release the distal end of the extension arm from the roller, whereby the support portion moves to the second position by operation of the first urging member.

8. The analysis device according to claim 7, wherein the extension arm comprises a proximal end configured to come in contact with the roller when the support portion is at the second position, and the proximal end of the extension arm is shaped to obliquely contact the roller so that a movement of the cover from the withdrawal prevention position to the withdrawal position will cause the roller to force the extension arm to move the support portion from the second position to the first position against the urging force of the first urging member.

9. The analysis device according to claim 4, wherein the suction pipe moving mechanism comprises a second urging member one end of which is attached to the suction pipe moving mechanism and the other end of which is attached to the suction pipe so that the second urging member will function to connect the suction pipe moving mechanism and the suction pipe at an adjustable distance between them.

10. The analysis device according to claim 1, wherein the cover includes a grasp portion arranged on a front surface side of the cover.

* * * * *